(12) United States Patent
Smith

(10) Patent No.: US 11,723,652 B2
(45) Date of Patent: Aug. 15, 2023

(54) SUTURING APPARATUS AND METHOD

(71) Applicant: Gyrus ACMI Inc., Southborough, MA (US)

(72) Inventor: Adam Lee Smith, Palm Desert, CA (US)

(73) Assignee: Gyrus ACMI, Inc., Westborough, MA (US)

( * ) Notice: Subject to any disclaimer, the term of this patent is extended or adjusted under 35 U.S.C. 154(b) by 126 days.

(21) Appl. No.: 17/034,183

(22) Filed: Sep. 28, 2020

(65) Prior Publication Data
US 2021/0093320 A1 Apr. 1, 2021

Related U.S. Application Data

(60) Provisional application No. 62/908,524, filed on Sep. 30, 2019, provisional application No. 62/908,503, (Continued)

(51) Int. Cl.
*A61B 17/04* (2006.01)
*A61B 17/11* (2006.01)
(Continued)

(52) U.S. Cl.
CPC ...... *A61B 17/0482* (2013.01); *A61B 17/0625* (2013.01); *A61B 17/06066* (2013.01); (Continued)

(58) Field of Classification Search
CPC .......... A61B 17/0482; A61B 17/06066; A61B 17/0625; A61B 17/11; A61B 2017/06076; (Continued)

(56) References Cited

U.S. PATENT DOCUMENTS 5,351,518 A * 10/1994 Bogart ..................... B21G 1/00
72/401
5,810,851 A 9/1998 Yoon
(Continued)

FOREIGN PATENT DOCUMENTS

CN 112568950 A 3/2021
DE 102020125257 A1 4/2021
(Continued)

OTHER PUBLICATIONS

"U.S. Appl. No. 17/034,267, Response filed Nov. 30, 2022 to Restriction Requirement dated Oct. 4, 2022", 7 pgs.
(Continued)

*Primary Examiner* — Tan-Uyen T Ho
*Assistant Examiner* — David P Stein
(74) *Attorney, Agent, or Firm* — Schwegman Lundberg & Woessner, P.A.

(57) ABSTRACT

Disclosed embodiments include apparatuses, systems, and methods for guiding a needle to facilitate suturing, such as in surgical anastomosis. In an illustrative embodiment, an apparatus includes a frame configured to counter-rotatably support two generally parallel rollers. A first roller supported by the frame has a flat surface configured to rollably engage a first face of a shaft of a helically-shaped needle. A second roller supported by the frame has a grooved surface defining a helical groove is configured to at least partially receive a second face of the shaft. The second roller further defines a correcting recess bounded by lateral surfaces at a forward end of the groove that tapers to a width of the groove at the forward end. When the leading end is received into the correcting recess, at least one of the lateral surfaces engages and guides the leading end into the forward end of the groove.

18 Claims, 24 Drawing Sheets

Related U.S. Application Data filed on Sep. 30, 2019, provisional application No. 62/908,554, filed on Sep. 30, 2019.

(51) Int. Cl.
*A61B 17/06* (2006.01)
*A61B 17/062* (2006.01)

(52) U.S. Cl.
CPC ..... *A61B 17/11* (2013.01); *A61B 2017/06076* (2013.01); *A61B 2017/1107* (2013.01)

(58) Field of Classification Search
CPC .. A61B 2017/1107; A61B 2017/00685; A61B 17/0469; A61B 2017/00398; A61B 2017/06052; A61B 17/0491; A61B 2017/0498
See application file for complete search history.

(56) References Cited

U.S. PATENT DOCUMENTS

| | | | |
|---|---|---|---|
| 6,015,416 A | 1/2000 | Stefanchik et al. | |
| 6,613,058 B1 | 9/2003 | Goldin | |
| 7,972,370 B2 | 7/2011 | Douk et al. | |
| 9,408,607 B2 | 8/2016 | Cartledge et al. | |
| 2003/0153931 A1 | 8/2003 | Schraft et al. | |
| 2006/0212048 A1* | 9/2006 | Crainich | A61B 17/0469 |
| | | | 606/144 |
| 2019/0343529 A1 | 11/2019 | Smith et al. | |
| 2021/0093315 A1 | 4/2021 | Smith | |
| 2021/0093319 A1 | 4/2021 | Smith | |

FOREIGN PATENT DOCUMENTS

| | | |
|---|---|---|
| GB | 2590138 A | 6/2021 |
| JP | 2021053393 A | 4/2021 |

OTHER PUBLICATIONS

"U.S. Appl. No. 17/034,267, Restriction Requirement dated Oct. 4, 2022", 6 pgs.

"United Kingdom Application Serial No. 2015166.8, Search Report dated Mar. 12, 2021", 3 pgs.

"United Kingdom Application Serial No. 2015166.8, Subsequent Examination Report dated Feb. 22, 2023", 3 pgs.

"U.S. Appl. No. 17/034,267, Non Final Office Action dated Mar. 16, 2023", 10 pgs.

* cited by examiner

SUTURING APPARATUS AND METHOD

PRIORITY CLAIM

The present application claims the priority and benefit of U.S. Patent Application Ser. Nos. 62/908,503, 62/908,524, 62/908,554, all of which are entitled "SUTURING APPARATUS AND METHOD" and were filed Sep. 30, 2019.

FIELD

The present disclosure relates to apparatuses, systems, and methods for suturing an object such as a juncture of two passages.

BACKGROUND

The statements in this section merely provide background information related to the present disclosure and may not constitute prior art.

Surgical anastomosis enables segments of one or more arteries, blood vessels, intestines, or any other passages to be connected or reconnected, such as in coronary artery bypass graft (CABG) procedures. In a CABG procedure, for example, a saphenous vein may be harvested from a patient's leg and grafted to circumvent a coronary arterial blockage. Such procedures are tremendously useful and may regularly save and extend lives.

However, CABG procedures and similar procedures involve highly invasive surgery. For example, a typical CABG procedure involves performing a median sternotomy in which a vertical incision is made along the patient's sternum, after which the sternum itself is actually broken open to provide access to the heart and surrounding arteries. The median sternotomy provides a surgeon with space to insert a graft and suture the graft to a coronary artery to complete the process. However, the sizable incision and the breaking of the sternum may involve significant scarring, discomfort, and risk of infection, and may require significant recovery time for the healing of the affected structures.

SUMMARY

Disclosed embodiments include apparatuses, systems, and methods for driving a needle to facilitate suturing, such as may be performed in a surgical anastomosis procedure involving veins, arteries, or other passages.

In an illustrative embodiment, an apparatus includes a frame. First and second rollers are rotatably mounted parallel with each other in the frame and are configured to engage therebetween a shaft of a needle formed in a helical shape. The first and second rollers are configured to counter-rotate. The needle is revolvable around the first roller responsive to counter-rotation of the first and second rollers. A drive mechanism is secured to the frame and is configured to move the frame.

In another embodiment, a system includes a needle formed in a helical shape, where the needle includes a shaft having a trailing end configured to draw a filament and a leading end shaped to pierce an object. A drive track is positionable to guide a path of the needle. A needle drive mechanism includes a frame. First and second rollers are rotatably mounted parallel with each other in the frame and are configured to engage therebetween a shaft of a needle formed in a helical shape. The first and second rollers are configured to counter-rotate. The needle is revolvable around the first roller responsive to counter-rotation of the first and second rollers. A drive mechanism is secured to the frame and is configured to move the frame along the drive track.

In a further illustrative embodiment, in an illustrative method opposing sides of a shaft of a needle are engaged between parallel faces of first and second rollers, where the needle is formed in a helical shape and configured to draw a filament from its trailing end. The first and second rollers are counter-rotated to cause the helically-shaped needle to revolve around the first roller positioned adjacent to an object to cause a leading end of the needle to pierce the object adjacent to an outer face of the first roller. The first and second rollers are translated along an edge of the object. Counter-rotating the first and second rollers and translating the first and second rollers causes the needle to draw the filament to suture the edge of the object adjacent the outer face of the first roller.

In another illustrative embodiment, an apparatus includes a frame configured to counter-rotatably support two generally parallel rollers. A first roller supported by the frame has a flat surface configured to rollably engage a first face of a shaft of a helically-shaped needle. A second roller supported by the frame has a grooved surface defining a groove that is configured to at least partially receive a second face of the shaft. The bottom of the groove has a bottom width at least as wide as the second face and bounded by sides extending to a groove opening at the grooved surface having a surface width that is wider than the second face.

In another embodiment, a system includes a helically-shaped needle, where the needle includes a shaft having a trailing end configured to draw a filament and a leading end shaped to pierce an object. A needle drive mechanism includes a frame configured to counter-rotatably support two generally parallel rollers across a gap. A first roller has a flat surface disposed to rollably engage a first face of a shaft of a helically-shaped needle. A second roller supported by the frame has a grooved surface defining a groove that is configured to at least partially receive a second face of the shaft. A bottom of the groove has a bottom width at least as wide as the second face and bounded by sides extending to a groove opening at the grooved surface having a surface width that is wider than the second face. A drive mechanism is secured to the frame and configured to counter-rotate the rollers and to move the frame along an edge of an object to be sutured by the filament.

In a further illustrative embodiment, in an illustrative method opposing faces of a shaft of a helically-shaped needle are engaged between a first roller and a second roller parallel with the first roller. The first roller includes a flat surface that engages a first face of the shaft and the second roller includes a grooved surface that defines a groove that at least partially receives a second face of the shaft within the groove. A bottom of the groove has a bottom width at least as wide as the second face and bounded by sides extending to a groove opening at the grooved surface having a surface width that is wider than the second face. The first and second rollers are counter-rotated to cause the helically-shaped needle to revolve around the first roller positioned adjacent to an object to cause a leading end of the needle to pierce the object adjacent to an outer face of the first roller. The first and second rollers are translated along an edge of the object. Counter-rotating the first and second rollers and translating the first and second rollers causes the needle to draw the filament to suture the edge of the object adjacent the outer face of the first roller.

In a still further embodiment, an apparatus includes a frame configured to counter-rotatably support two generally parallel rollers. A first roller is supported by the frame, the first roller having a flat surface configured to rollably engage a first face of a shaft of a helically-shaped needle. A second roller is supported by the frame, the second roller having a grooved surface defining a helical groove that is configured to at least partially receive a second face of the shaft. The second roller further defines a correcting recess bounded by lateral surfaces at a forward end of the groove that tapers to a width of the groove at the forward end of the groove. When the leading end is received into the correcting recess responsive to counter-rotation of the first and second rollers, at least one of the lateral surfaces engages and guides the leading end into the forward end of the groove.

In still another embodiment, a system includes a helically-shaped needle, where the needle includes a shaft having a trailing end configured to draw a filament and a leading end shaped to pierce an object. A frame is configured to counter-rotatably support two generally parallel rollers. A first roller is supported by the frame, the first roller having a flat surface configured to rollably engage a first face of a shaft of a helically-shaped needle. A second roller is supported by the frame, the second roller having a grooved surface defining a helical groove that is configured to at least partially receive a second face of the shaft. The second roller further defines a correcting recess bounded by lateral surfaces at a forward end of the groove that tapers to a width of the groove at the forward end of the groove. When the leading end is received into the correcting recess responsive to counter-rotation of the first and second rollers, at least one of the lateral surfaces engages and guides the leading end into the forward end of the groove. A drive mechanism is secured to the frame and configured to counter-rotate the rollers and to move the frame along an edge of an object to be sutured by the filament.

In still another embodiment, in an illustrative method, a helically-shaped needle is counter-rotatably motivated between a grooved roller and an opposing flat roller. A leading end of the needle is received in a correcting recess at a forward end of a helical groove defined by a grooved roller. The leading end of the needle is engaged by at least one lateral surface of the correcting recess. The leading end of the needle is guided along the at least one lateral surface into the forward end of the helical groove.

In a further embodiment, an apparatus includes at least one guide member configured to extend from a suturing mechanism, where the suturing mechanism is configured to revolve a helically-shaped needle around an axis while the needle is advanced around an object to be sutured. A guide track is configured to be positioned around the object and to guide the suturing mechanism in an articulated path around the object. The guide track defines at least one guide channel configured to receive the guide member. The at least one guide channel is configured to direct movement of the guide member to cause the suturing mechanism to pivot to realign the axis to be tangential to the curved guide track.

In still embodiment, a system includes a helically-shaped needle configured to draw a filament from a trailing end. A suturing mechanism is configured to revolve the needle around an axis while rollably advancing the suturing mechanism around an object to be sutured and supporting at least one guide member. A guide track is configured to be positioned around the object and to guide the suturing mechanism in an articulated path around the object. The guide track defines at least one guide channel configured to receive the guide member. The at least one guide channel is configured to direct movement of the guide member to cause the suturing mechanism to pivot to realign the axis to be tangential to the curved guide track.

In still another embodiment, in an illustrative method a suturing mechanism is rollably advanced around a curved path, the suturing mechanism being configured to cause a helically-shaped needle to revolve around an axis. The needle is revolved to cause a leading end and a trailing end of the needle to pass through a body. The suturing mechanism is guided along an articulated path to cause the suturing mechanism to pivot at locations around the curved path where the leading end and the trailing end of the needle are clear of the body to realign the axis to be tangential with the curved path before the leading end of the needle next pierces the body.

Further features, advantages, and areas of applicability will become apparent from the description provided herein. It will be appreciated that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings.

DETAILED DESCRIPTION

It will be noted that the first digit of three-digit reference numbers corresponds to the figure number in which the element first appears.

The following description explains, by way of illustration only and not of limitation, various embodiments of noninvasive apparatuses, systems, and methods for suturing an object, such as a juncture of passages being joined together in a surgical anastomosis procedure.

Figure 1:
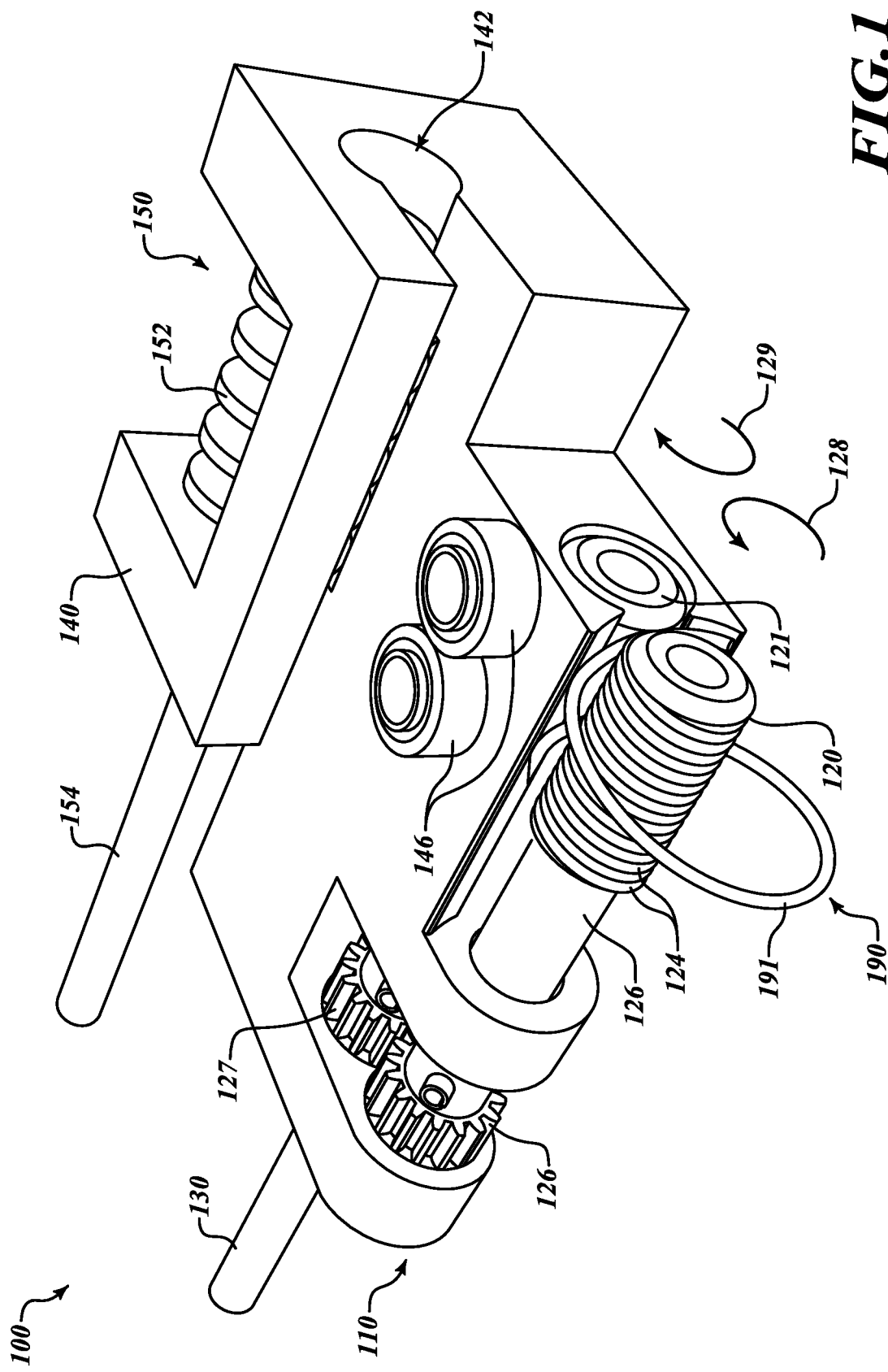
FIG. 1 is a perspective view of an embodiment of an apparatus for suturing an object with a helically-shaped needle.

Given by way of non-limiting overview and referring to FIG. 1, in various embodiments an apparatus 100 includes a frame 110. Rollers 120 and 121 are rotatably mounted parallel with each other in the frame 110 and are configured to engage therebetween a shaft 191 of a needle 190 formed in a helical shape. The rollers 120 and 121 are configured to counter-rotate. The needle 190 is revolvable around the roller 120 responsive to counter-rotation of the rollers 120 and 121. A drive mechanism 150 is secured to the frame 110 and is configured to move the frame 110.

Now that an overview has been given, details of various embodiments will be explained by way of non-limiting examples given by way of illustration only and not of limitation.

Still referring to FIG. 1, in various embodiments, the apparatus 100 may be well suited for suturing together passages or other objects. In such embodiments, the frame 110 is adapted for supporting the rollers 120 and 121. The rollers 120 and 121 are configured to drive the needle 190 to draw a filament to suture one or more objects (not shown in FIG. 1). In the example of a CABG procedure, the objects may include an end of a donor passage and an opening in a receiving passage that may be joined together with sutures to complete an anastomosis procedure. In various embodiments, the apparatus 100 is adapted to be compact for insertion into a bodily cavity, for example, by insertion into a patient's chest cavity via a subxiphoid incision made below a sternum of the patient (not shown). It will be appreciated that insertion of the apparatus 100 inserted through a relatively minor incision for use in suturing may help contribute to reducing potential trauma, risk, and protracted healing process that may result from performance of a median sternotomy, as commonly may be used to perform the implantation and suturing of a donor vein in a conventional CABG procedure.

However, it will be appreciated that use of the apparatus 100 is not limited to CABG procedures. Given by way of non-limiting examples, the apparatus 100 may be used for suturing in other procedures, such as without limitation, forming suturing an arteriovenous fistula between an artery and a vein for dialysis, suturing a colostomy formed between the bowel and the skin of the abdominal wall, or in coupling ends of intestinal sections when a formerly intervening portion has been removed. As such, it will be appreciated that no such limitations are intended and are not to be inferred.

In various embodiments, recesses in the frame 110 receive the rollers 120 and 121, as further described below with reference to FIG. 2. The recesses in the frame enable the rollers 120 and 121 to rotate and to be driven by an external source of rotational force. Although only the roller 120 is exposed in FIG. 1, the roller 121 may have a structure similar to that of the roller 120, as described below with reference to FIG. 2. The roller 120 includes a cylinder 122 which defines a number of grooves 124 that are sized and shaped to engage the shaft 191 of the needle 190. Specifically, the grooves 124 are shaped to have a width and cross-sectional shape to at least partially receive the shaft 191 of the needle 190. The grooves 124 also are angled to accommodate a pitch of the needle 190. The width and pitch of the grooves 124 are further described below with reference to FIG. 2. In various embodiments, the cylinder 122 of the roller 120 may also define feature the grooves 124, while the roller 121 may have a generally smooth surface or generally textured surface configured to press the needle 190 into the grooves 124 of the roller 120.

In various embodiments, drive gears 126 and 127 are configured to engage the rollers 120 and 121, respectively. In some embodiments, the drive gears 126 and 127 may be coupled with the rollers 120 and 121, respectively. In some other embodiments, the drive gears 126 and 127 may be integrally formed as part of the rollers 120 and 121, respectively. The drive gears 126 and 127 are interleaved so that rotation of the roller 120 in a first direction causes the roller 121 to counter-rotate in a second, opposite direction. As a result, imparting a rotational force to the roller 121, for example, causes the roller 121 to rotate in a first rotational direction (as indicated by an arrow 128) and cause the roller 120 to counter-rotate in a second rotational direction (as indicated by an arrow 129 that is opposite the first rotational direction). A rotatable member 130, such as a drive shaft or a drive cable, may be directly mechanically coupled to the roller 120 or the roller 121 to provide rotational force to one of the rollers 120 and 121 to cause the rollers 120 and 121 to counter-rotate.

In various embodiments, the needle 190 has a radius larger than that of the roller 120 around which the needle 190 rotates. Thus, when the shaft 191 of the needle 190 is engaged between the rollers 120 and 121, an axis of the needle 190 and an axis of the roller 120 are not colinear. As a result, rotation of the needle 190 (caused by the counter-rotation of the rollers 120 and 121) causes the needle 190 to rotate around the roller 120. The rotation of the needle 190 around the roller 120 enables the rollers 120 and 121 to drive the needle 190, thereby causing the needle 190 to repeatedly pierce an object (not shown in FIG. 1) that is adjacent to the roller 120.

In various embodiments, the apparatus 100 may be adapted to follow a drive track (not shown in FIG. 1) that guides the apparatus 100 to operate along a particular course around an object to be sutured (not shown in FIG. 1). In such embodiments, a guide bracket 140 may be disposed on the frame 110. The guide bracket 140 defines an internal guide 142 that is shaped to receive an edge of the drive track so as to hold the frame 110 onto the drive track. The guide bracket 140 also may be configured to receive a drive mechanism 150 and to hold the drive mechanism 150 against the drive track to enable the drive mechanism 150 to motivate the apparatus 100 along the drive track. The frame 110 may include one or more transverse rollers 146 that are configured to rollably engage the drive track to hold the frame 110 to the drive track. The transverse rollers 146 may be mounted on the frame 110 on or adjacent to the guide bracket 140 as shown in FIG. 1.

In various embodiments, the drive mechanism 150 includes a worm gear 152 that is pitched so that rotation of the worm gear 152 moves the apparatus 100 along the drive track. In some embodiments, the worm gear 152 is configured to engage a rotatable drive member 154 that provides rotational force to the worm gear 152. In some other embodiments, the worm gear 152 may be engaged through one or more gears (not shown in FIG. 1) with the rotatable member 130 or one or more of the rollers 120 and 121 to provide rotational force to the worm gear 152.

Figure 2:
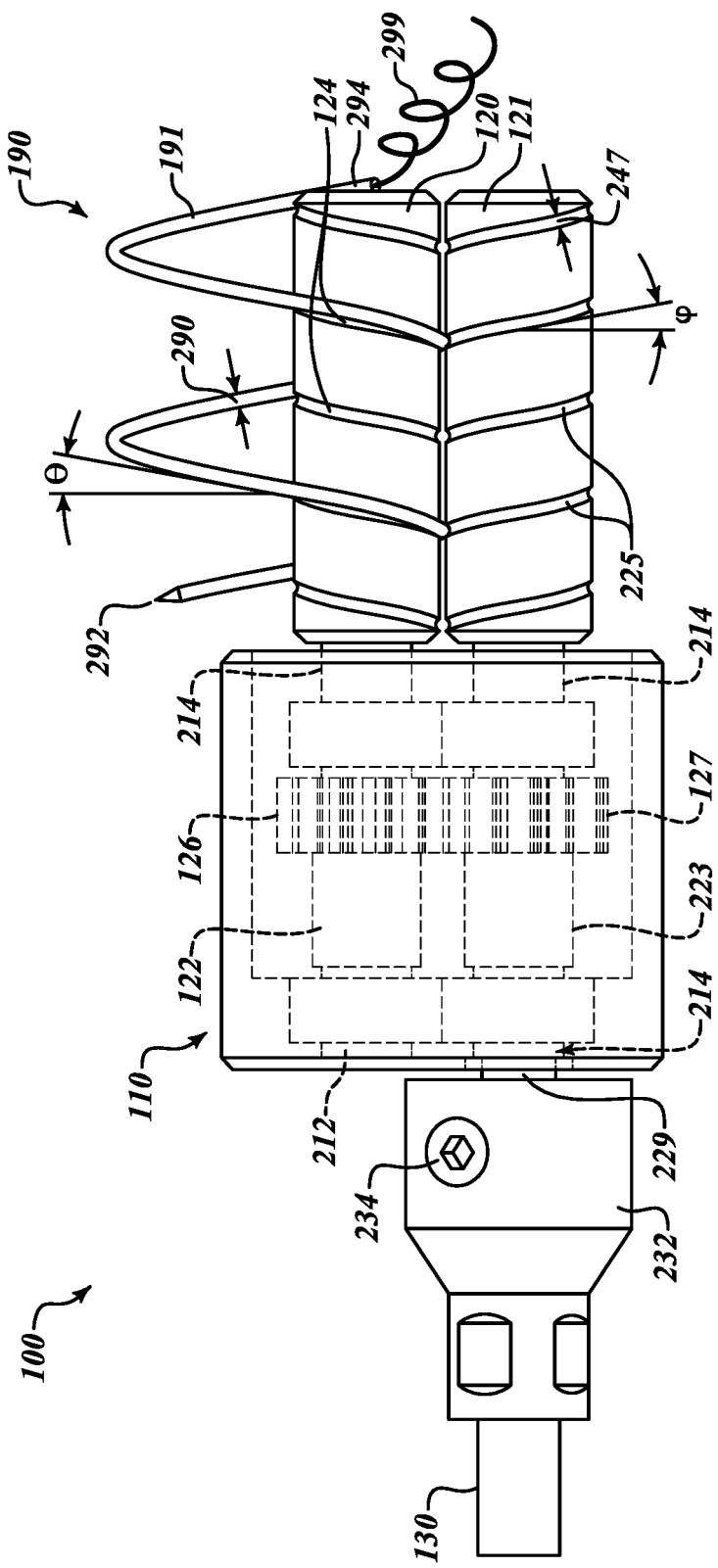
FIG. 2 is a perspective view in partial cutaway form of the apparatus of FIG. 1.

Referring additionally to FIG. 2, in various embodiments both the rollers 120 and 121 include grooves 124 and 225, respectively, to engage the shaft 191 of the needle 190. As shown in FIG. 2, the grooves 124 and 225 are pitched in opposite directions to pinchably and rollably engage the shaft 191 of the needle 190. A width 247 of the grooves 124 and 225 is sized to releasably engage a width 290 of the shaft 191 of the needle 190. A pitch $\varphi$ of the grooves 124 and 225 matches a pitch $\theta$ of the needle 190. The corresponding widths 247 and 290 and corresponding pitches $\varphi$ and $\theta$ enable the rollers 120 and 121 to drive rotation of the needle 190 around the roller 120 as the rollers 120 and 121 counter-rotate. The needle 190 itself includes a leading end 292 that is shaped to pierce an object or objects, such as without limitation tissues that may include edges of donor and receiving passages to be sutured together by the apparatus 100 (FIG. 1). The needle 190 also may include a trailing end 294 configured to receive or to be attached to a filament 299 that is used to suture together the object.

Still referring to FIG. 2, the rollers 120 and 121 include cylinders 122 and 223, respectively, that are rotatably received in the frame 110. At one end, the cylinders 122 and 223 may be rotatably received in cylindrical openings 214 that extend through the frame 110. At an opposing end, each of the cylinders 122 and 223 may be received in a rounded recess 212 or in a cylindrical opening 214. In some embodiments the cylindrical opening 214 may enable a drive shaft 229, that is fixably coupled with the roller 121, to extend through the frame 110. In such embodiments, the drive shaft 229 may thus engage the rotatable member 130, thereby providing rotational force to the roller 121. The rotational force is also provided to the roller 120 via the interleaved drive gears 126 and 127, thereby causing the roller 120 and the roller 121 to counter-rotate. It will be appreciated that, in some other embodiments, the drive shaft 229 may be fixably coupled with the roller 120 such that the interleaved drive gears 126 and 127 impart rotational force to the roller 121, thereby causing the roller 120 and the roller 121 to counter-rotate.

In various embodiments, the rotatable member 130 may be mechanically joined to the drive shaft 229 by a coupling 232 which may be securable and removable by an attachment device 234, such as without limitation an inset screw. The rotatable member 130 may be driven by a motor (not shown in FIG. 2) that is disposed external to the apparatus 100. The cylindrical openings 214 and/or the rounded recess 212 may include bushings (not shown in FIG. 2) formed of nylon or other materials to reduce friction and/or vibration between the rollers 120 and 121 and the frame 110 and/or between the drive shaft 229 and the frame 110.

Figure 3:
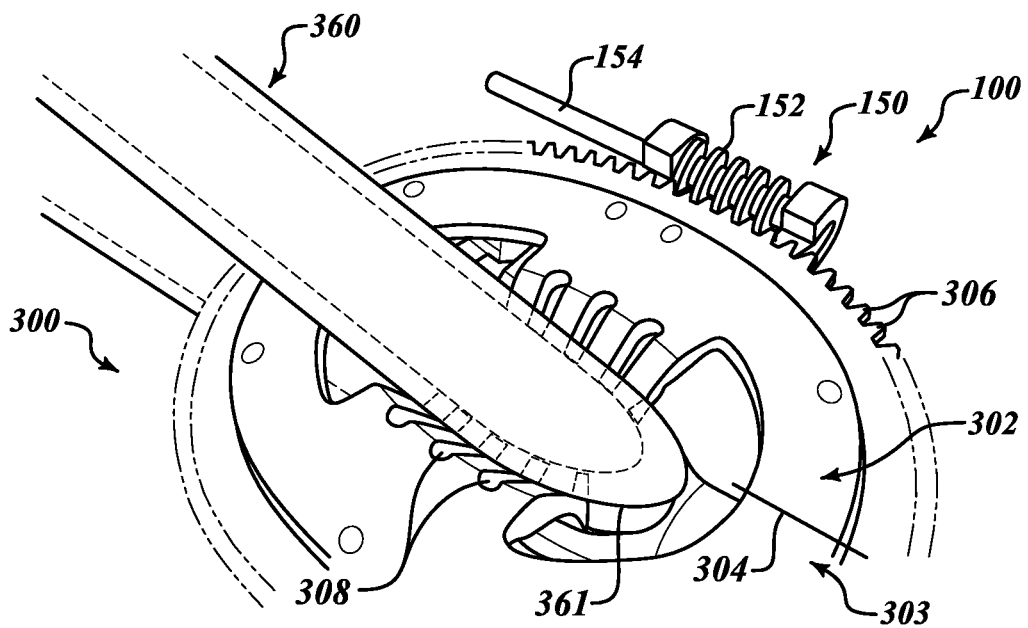
FIGS. 3 and 4 are top and bottom perspective views, respectively, of the apparatus of FIG. 1 positioned on a drive track for guiding the apparatus of FIG. 1.

Referring additionally to FIG. 3, in various embodiments a drive track 300 is used to guide the apparatus (not shown in FIG. 3) around an object to be sutured. FIG. 3 shows a donor passage 360 having a distal edge 361 to be joined to a receiving passage (not shown in FIG. 3) as in an anastomosis procedure. The drive track 300 may include separate sections 302 and 303 that may be positioned around an object, such as the donor passage 360, and then mechanically coupled at a junction 304. The drive track 300 supports teeth 306 that are shaped and sized to be engaged by the worm gear 152. In various embodiments, rotational force imparted by the rotational drive member 154 drives the worm gear 152 and, thus, causes the worm gear 152 to translate the apparatus 100 along the guide track 300. The interaction of the worm gear 152 and the drive track 300 thus causes the apparatus 100 to translate along an edge of the object, such as the distal end 361 of the donor passage 360. In various embodiments, the drive track 300 includes inner channels 308 defined along the object that enable the needle (not shown in FIG. 3) to extend from the apparatus 100 to and through the object.

Figure 4:
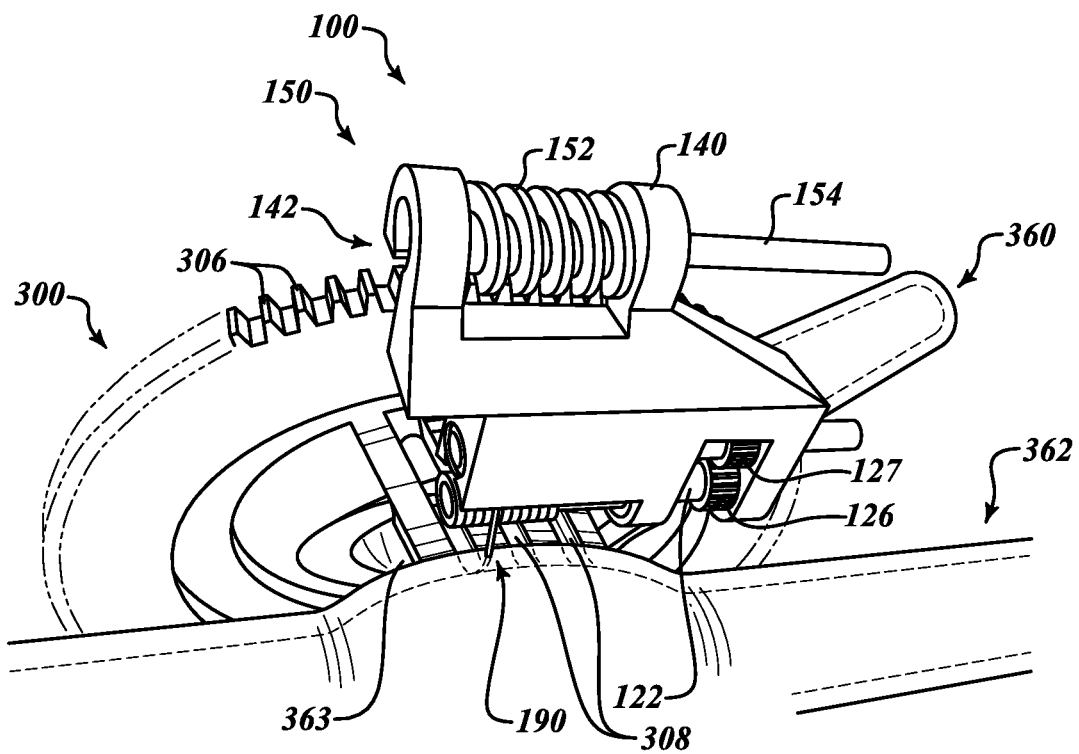

Referring additionally to FIG. 4, the guide bracket 140 of the frame 110 guides the apparatus 100 along the drive track 300. The receiving passage 362 defines an opening 363 beneath the drive track 300. The guide bracket 140 engages the drive track 300, and the drive track 300 is received in the internal guide 142 defined by the guide bracket 140. As previously described, the guide bracket 140 holds the worm gear 152 against the teeth 306 of the drive track 300. As a result, rotational force imparted to the worm gear 152 by the rotational drive member 154 causes the worm gear 152 to move the apparatus 100 around the drive track as the needle 190 passes through the channels 308 in the drive track 300 to suture the object.

Figure 5:
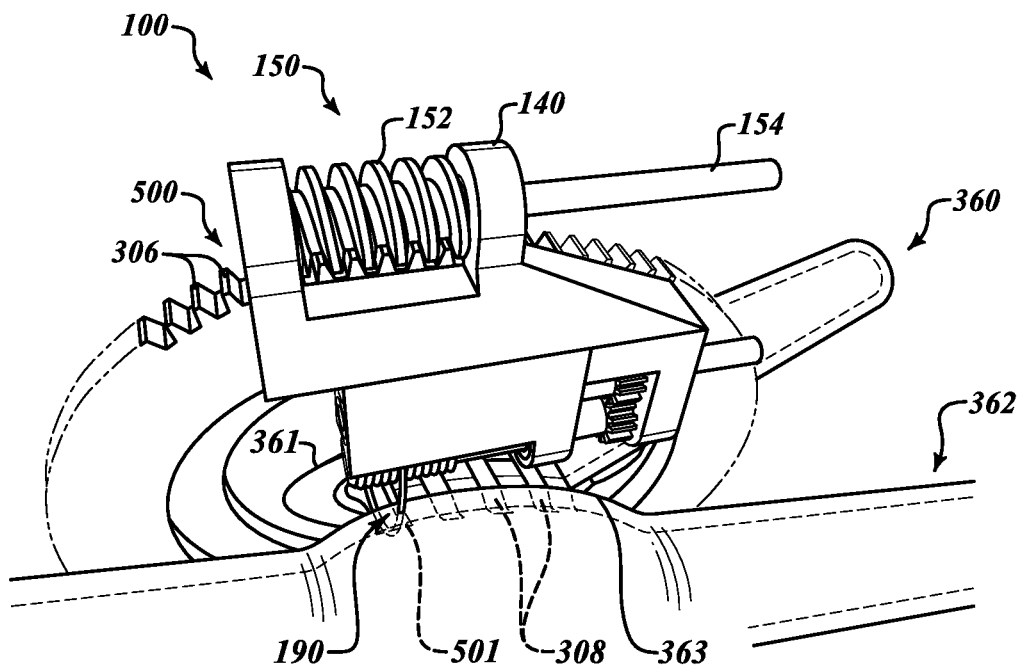
FIGS. 5 and 6 are views of the apparatus of FIG. 1 at different locations along the guide track of FIGS. 3 and 4 to illustrate a process of suturing using the apparatus of FIG. 1.
Figure 6:
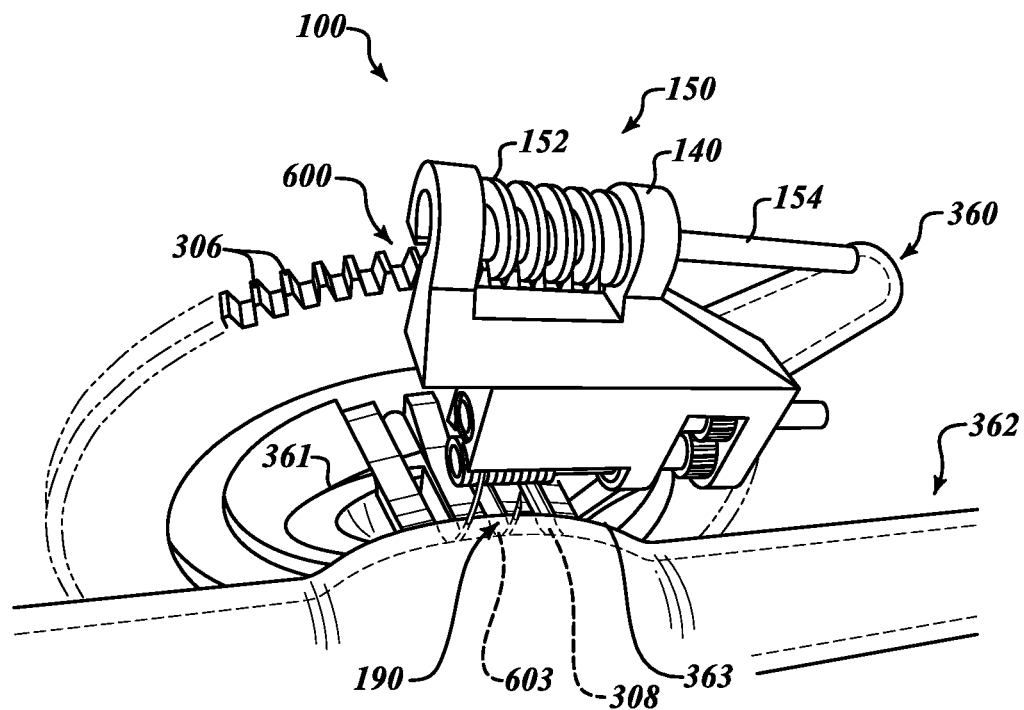

Referring additionally to FIGS. 5 and 6, the apparatus 100 moves around the drive track 300 as the needle 190 is rotated to suture the object. As shown in FIG. 5, the apparatus 100 is situated at a first point 500 along the drive track 300, and the needle 190 extends through a first channel 501 in the drive track 300. As shown in FIG. 6, rotation of the worm gear 152 has moved the apparatus 100 along the guide track 300 to a second point 600 while the needle 190 has been rotated. As a result, the needle 190 now extends through a second channel 603 in the drive track 300. The motion of the apparatus 100 around the guide track 300 as the needle 190 is rotated through an object thus sutures the object (which in this non-limiting example is a juncture of the donor passage 360 and the receiving passage 362).

It will be appreciated that, as shown in FIGS. 3-6, the drive track 300 suitably is a rounded track configured to lead the apparatus 100 around an object to suture the object, for example, to join passages together. However, it will be appreciated that a linear drive track may be used to form a linear suture, for example, to close a wound or incision. Thus, it will be appreciated that disclosed embodiments are not intended to be limited to a drive track 300 of any particular shape or size and no such limitation is to be inferred.

Figure 7:
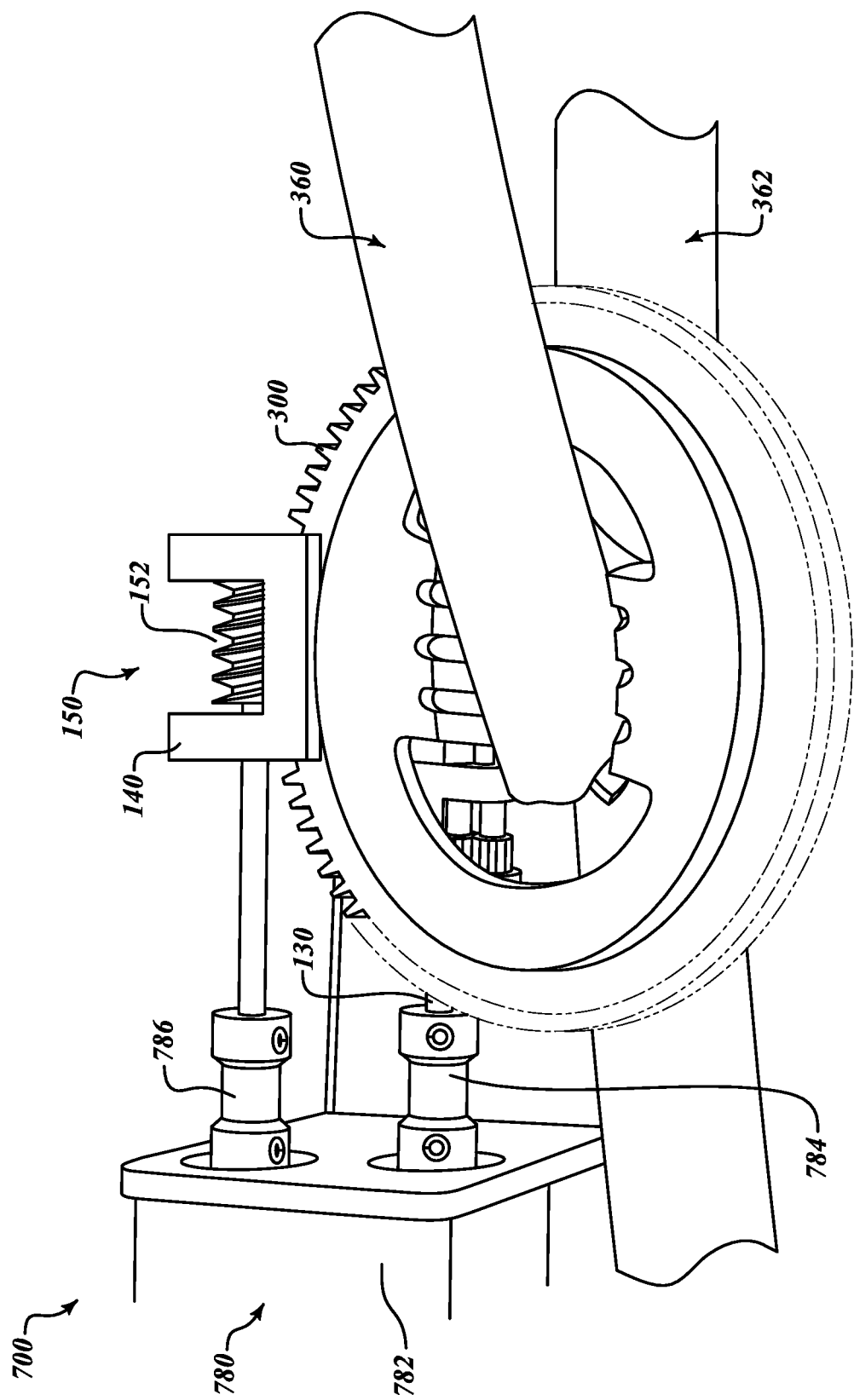
FIG. 7 is a perspective view of a system having a motor to impart rotational force to the apparatus of FIG. 1.

Referring additionally to FIG. 7 and in various embodiments, in an illustrative system 700 the drive track 300 is positioned around the object or objects to be sutured. A motor 780 provides rotational force to rotate the rollers 120 and 121 (not shown in FIG. 7) and to drive the worm gear 152. In various embodiments, a single motor 780 or multiple motors (not shown) may be used to provide rotational force to the rollers 120 and 121 and the worm gear 152 of the drive mechanism 150. The motor 780 may include a gearbox 782 so that, as desired, the single motor 780 may provide rotational force at different speeds to the rotational member 130 that is coupled with the rollers 120 and 121 and the rotational drive member 154 that is coupled to the worm gear 152 of the drive mechanism 150. The system 700 may include drive linkages 784 and 786 to connect with the rotational member 130 and the rotational drive member 154. The drive linkages 784 and 786 may include flexible drive cables to provide rotational force while accommodating motion and positioning of the apparatus 100.

In various embodiments and as shown in FIG. 7, the gearbox 782 may be positioned at or adjacent to the motor 780 with multiple drive linkages 784 and 786 extending to the rollers 120 and 121 and to the drive mechanism 150. In some other embodiments, the gearbox 782 may be positioned at the apparatus 100 so that rotational force imparted to one of the rollers 120 and 121 may be mechanically conveyed to the drive mechanism 150 or vice versa. As a result, with only a single linkage extending from the motor 780 to the apparatus, in such embodiments, rotational force may be provided to both the rollers 120 and 121 and to the drive mechanism 150.

Figure 8:
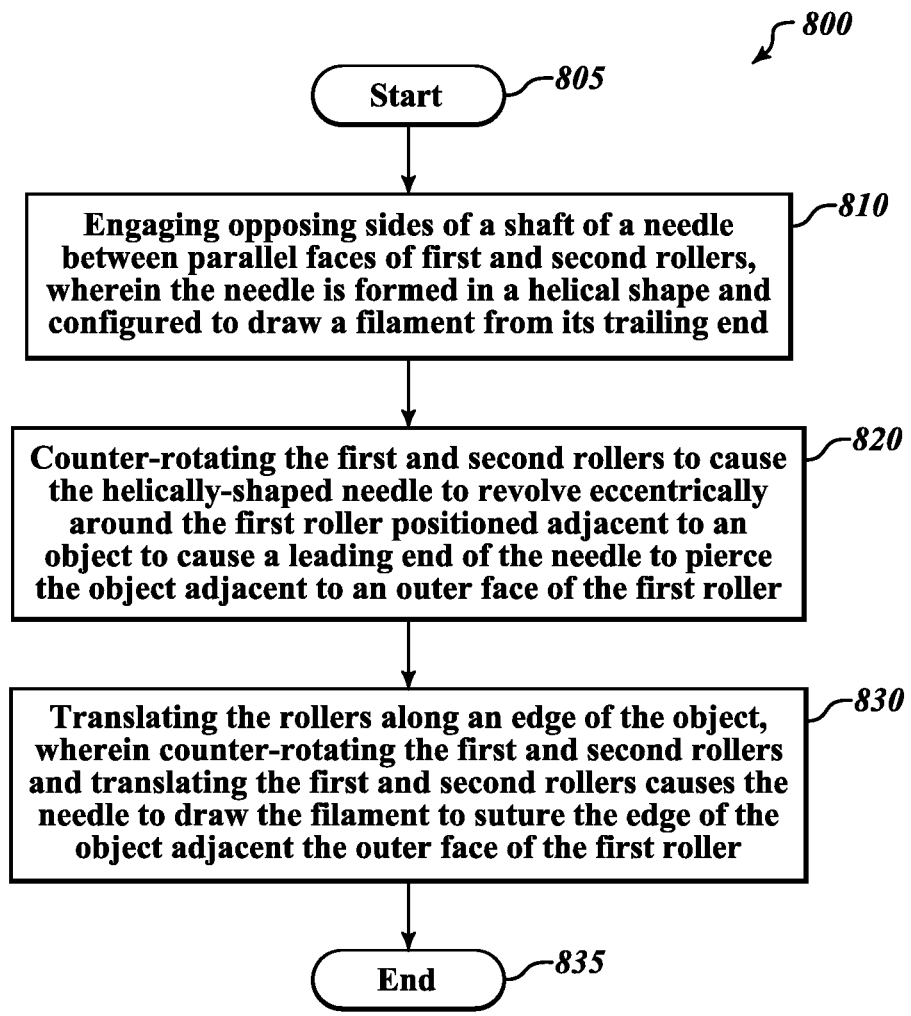
FIG. 8 is a flow diagram of an illustrative method of suturing an object.

Referring additionally to FIG. 8, in various embodiments, an illustrative method 800 of suturing an object, such as in an anastomosis, is provided. The method 800 starts at a block 805. At a block 810, opposing sides of a shaft of a needle are engaged between parallel faces of first and second rollers, where the needle is formed in a helical shape and is configured to draw a filament from its trailing end. At a block 820, the first and second rollers are counter-rotated to cause the helically-shaped needle to revolve around the first roller that is positioned adjacent to an object. Counter-rotation of the first and second rollers causes a leading end of the needle to pierce the object adjacent to an outer face of the first roller. At a block 830, the first and second rollers are translated along an edge of the object. Counter-rotating the first and second rollers and translating the first and second rollers causes the needle to draw the filament to suture the edge of the object adjacent the outer face of the first roller. With the object sutured, the method 800 ends at a block 835.

Referring back to FIG. 2, in various embodiments both the rollers 120 and 121 include grooves 124 and 225, respectively, to engage the shaft 191 of the needle 190. By contrast, in other embodiments, only one of the rollers may include a grove to engage the shaft 191 of the needle 190.

Figure 9:
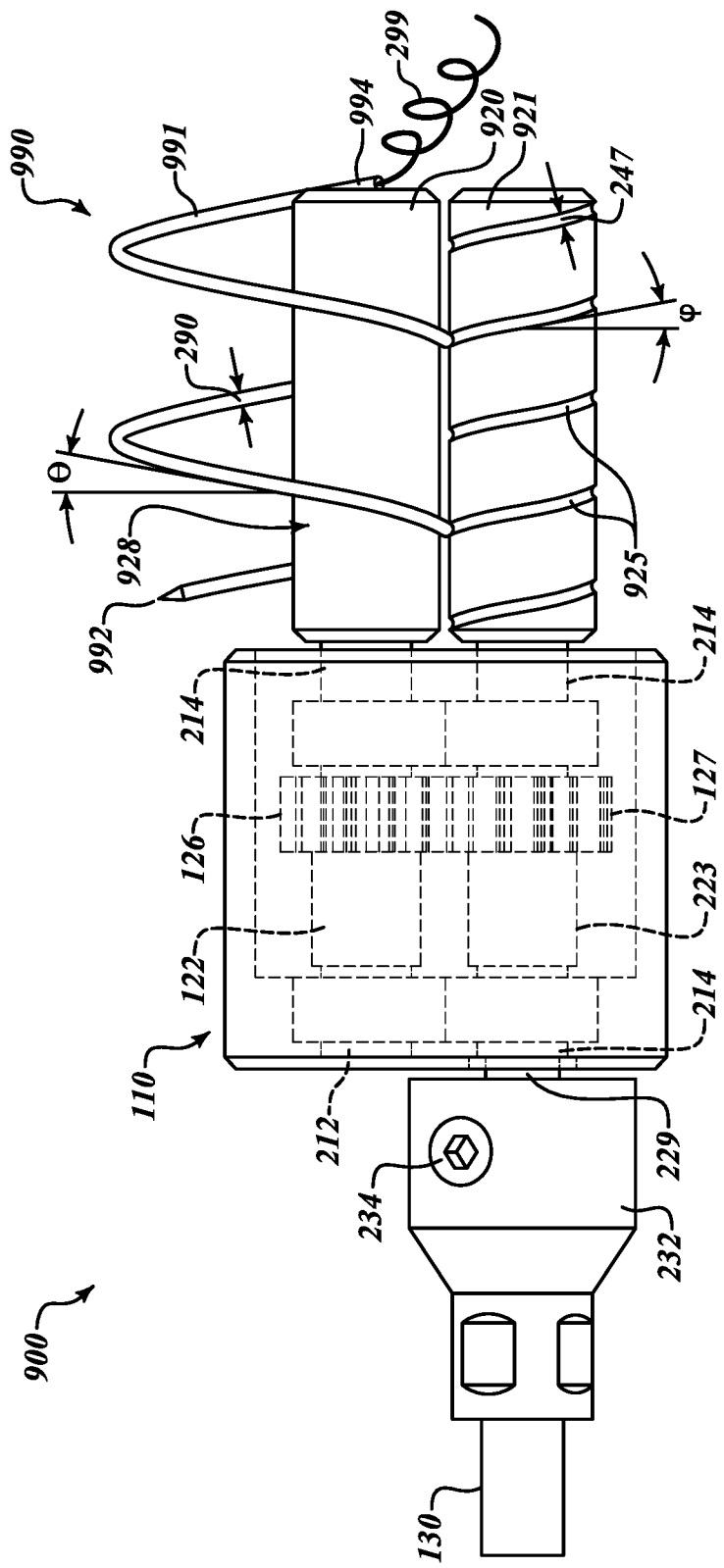
FIG. 9 is a perspective view in partial cutaway form of another embodiment of an apparatus for suturing an object with a helically-shaped needle.

Referring to FIG. 9, an apparatus 900 includes many of the same components and operates in the same manner as the apparatus 100 as described with reference to FIG. 2—with one exception. In the apparatus 900, a roller 921 includes a groove 925 that winds around the surface of the roller 121 to engage one side of a shaft 991 of the needle 990. As with the apparatus 100 of FIG. 2, a pitch of the groove 925 is angled to correspond with the pitch of the needle 990, as further described below. However, in contrast to the apparatus 100 of FIG. 2, a surface 928 of an opposing roller 920 does not include or define a groove to receive the needle 990.

As in the apparatus 100 of FIG. 2, the shaft 991 of the needle 990 is again frictionally engaged on opposing sides by the rollers 920 and 921. By contrast, in the apparatus 100 of FIG. 2, the shaft 191 of the needle 190 was engaged on both sides by grooves 124 and 225 of the rollers 120 and 121, respectively. In the apparatus 900 of FIG. 9, however, the shaft 991 of the needle 990 is frictionally engaged by the surface 928 of roller 920 on one side and the groove 925 of the roller 921 on the opposite side. As with the apparatus 100 of FIG. 2, frictional engagement of the rollers 921 and 920 with opposing sides of the shaft 991 of the needle 990 while the rollers 921 and 920 counter-rotate causes the needle 990 to revolve. Also like the apparatus 100 of FIG. 2, the revolution of the needle 990 causes the leading end 992 of the needle 990 to pierce an object to be sutured by a filament 299 drawn by a trailing end 994 of the needle 990.

As previously described with reference to FIG. 2, a pitch tri of the grooves 925 matches a pitch θ of the needle 990 so that the needle 990 fits within the grooves 921. It will be appreciated that the needle 990 has a larger radius about its axis than does the roller 921, and, as shown in FIG. 9, the roller 921 does not engage the needle 990 in every turn of the groove 925 at one time, and the roller 921 may revolve multiple times for each revolution of the needle 990. Thus, while the pitch tri of the grooves 925 corresponds with the pitch θ of the needle 990 so as to receive the needle 990 when the needle 990 revolves back into the groove 925, it will be appreciated that this does not mean that the pitch tri of the grooves 925 is equal to the pitch θ of the needle 990.

Figure 10:
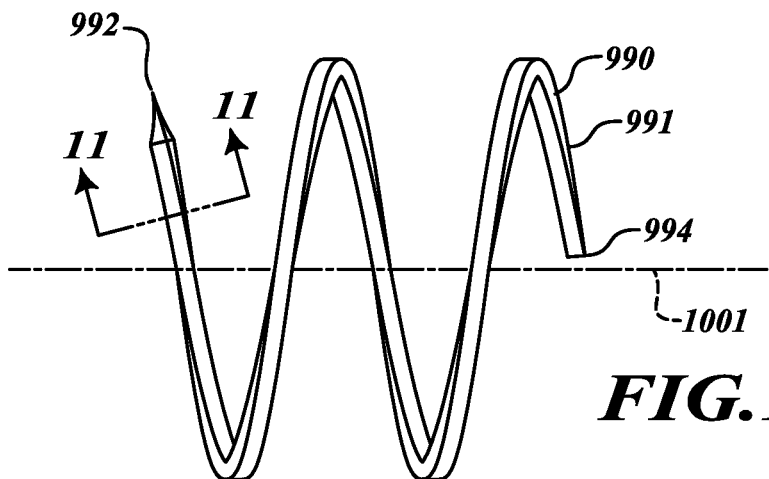
FIG. 10 is a side view of a helically-shaped needle used in conjunction with the apparatus of FIG. 9.

Referring to FIG. 10, the helical needle 990 has an axis 1001 about which it revolves when motivated by the counter-rotating rollers 920 and 921 (FIG. 9). As shown below in FIG. 12 and as in the case of the apparatus 100 of FIG. 2, the axis 1001 is not positioned coaxially with axes of either of the rollers 920 and 921. Instead, the axis 1001 is parallel with the axes of the rollers 920 and 921, thereby enabling the needle 990 to be revolved by the rollers 920 and 921 while rotating about its own axis 1001 to engage the body to be sutured (not shown in FIG. 9) on a side of the needle 990 opposite that where the needle is engaged by the rollers 920 and 921. In various embodiments, the shaft 991 of the needle 990 may have a rectangular or square cross-section, as described further below.

Figure 11:
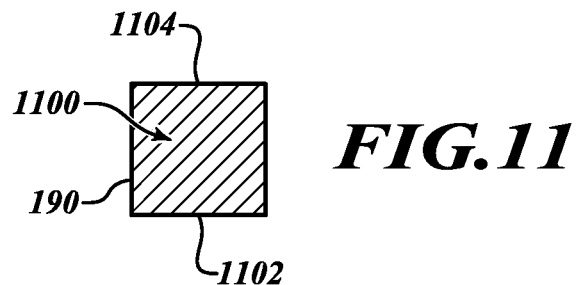
FIG. 11 is a cross-sectional view of the needle of FIG. 10.

Referring to FIG. 11, in a section of the shaft 991 of the needle 990 taken along axis 10-10 of FIG. 10, the shaft 991 of the needle 990 has opposing flat surfaces 1102 and 1104 that bound opposing sides of a generally rectangular or square cross-section 1100. The opposing flat surfaces 1102 and 1104 are engageable on one side within a groove 925 of the roller 921 and, on the other side, by the surface 928 of the roller 920.

Figure 12:
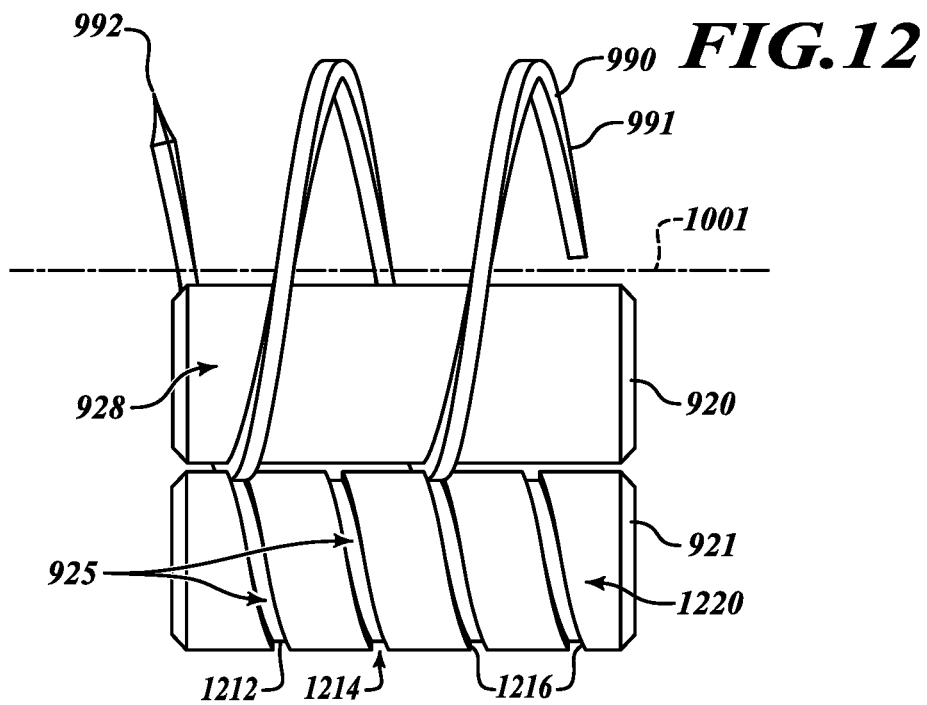
FIG. 12 is a schematic view of the rollers of the apparatus of FIG. 9 engaging the needle of FIG. 11.

Referring to FIG. 12, the shaft 991 of the needle 990 is received within a rectangularly-shaped groove 925 of the roller 921. The rectangularly-shaped groove 925 is bounded by a generally flat bottom 1212 that is bounded by generally flat sides 1216 that each extend to an opening 1214 at a grooved surface 1220 of the roller 921.

Figure 13:
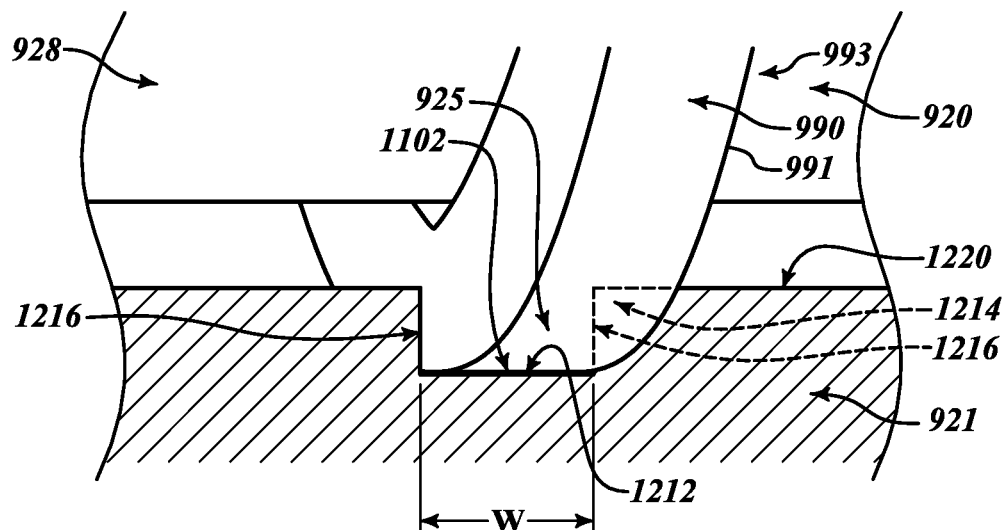
FIG. 13 is a schematic view of the rollers of FIG. 12 engaging the needle in a rectangularly-shaped groove.

Referring to FIG. 13, the shaft 991 of the needle 990 is received within the groove 925 in the roller 921. The shaft 991 of the needle 990 is received through the opening 1212 of the groove 925 of the roller 921. The flat surface 1102 on a side of the shaft 991 of the needle 990 is engaged by the generally flat bottom 1212 of the groove 925 between the generally flat sides 1216 of the groove 925. The surface 928 of the opposing roller 920 engages an opposite side of the shaft 991 of the needle 990 and presses the shaft 991 of the needle 990 into the groove 925 such that the shaft 991 of the needle 990 is frictionally engaged on both sides.

In various embodiments, the bottom 1212 of the groove 925 has a width W sized to be larger than a width of the flat surface 1102 on the side of the shaft 991. Because the needle 990 is helically-shaped, the shaft 991 angles away from the flat surface 1102 on an edge of the needle 990. The width W being larger than the width of the flat surface 1102 allows the helically-shaped needle 990 to be received within the groove 925 without the sides 1216 of the groove 925 impinging upon sides 993 of the shaft 991 of the needle 990.

Figure 14:
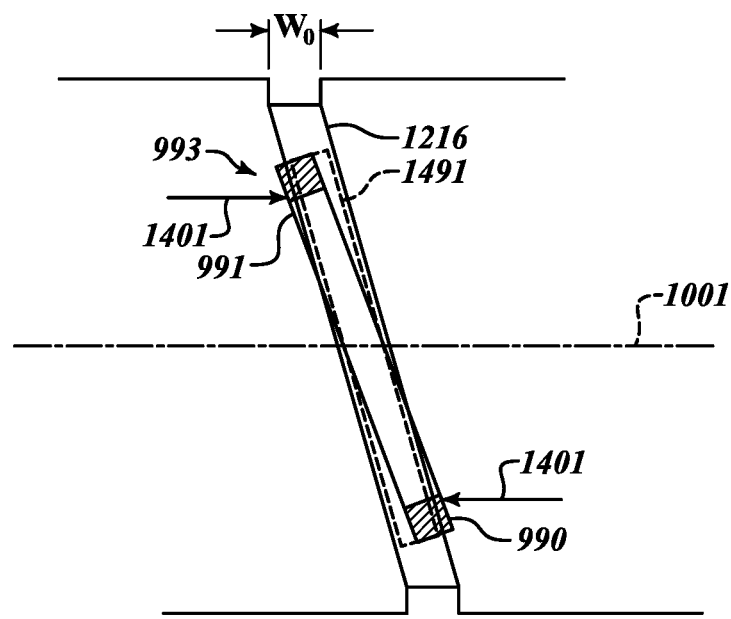
FIG. 14 is a schematic view of sides of the groove impinging upon and applying forces against the shaft of the needle.

Referring to FIG. 14, without the groove 925 having a width W wider than the flat surface 1102 on the edge of the needle 990, the sides 1216 of the groove 925 impinging upon sides 993 of the shaft 991 of the needle 990 may undesirably deform the needle 990. If the groove has a width Wo equal to or only slightly larger than of the flat surface 1102 on the edge of the needle 990, as the needle 990 is pressed into the groove by the opposing roller 920 (not shown in FIG. 14), the sides 1216 of the groove 925 will apply a force 1401 to the sides 993 of the shaft 991 of the needle 990. The force 1401 may compress the helically-shaped needle 990 along its axis 1001, resulting of a realigned form 1491 of the needle 990 twisted to fit the groove 925. Compression of the needle 990 may result in the relative pitches φ and θ of the groove 925 and the needle 990, respectively, no longer matching, thereby impeding the ability of the groove 925 to guide the needle 990, or other undesirable effects.

Figure 15:
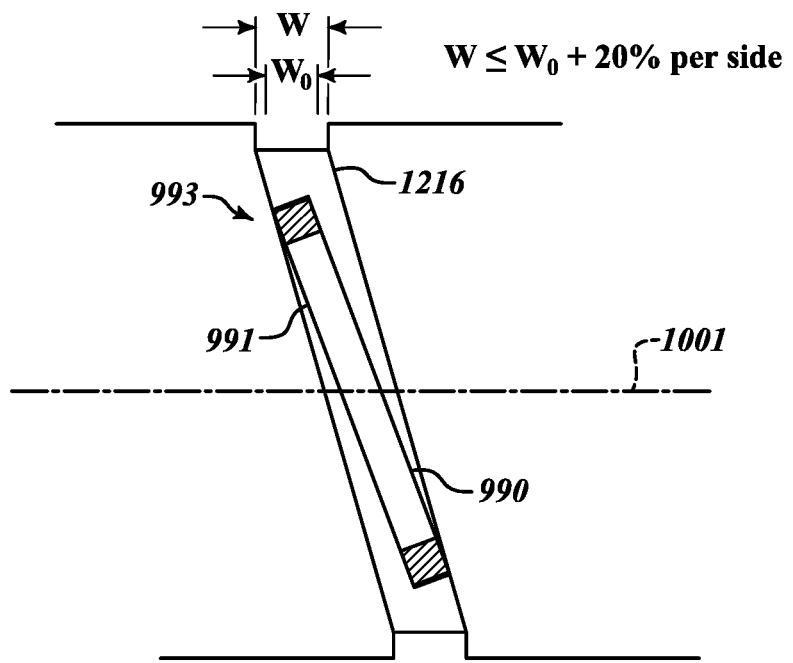
FIG. 15 is a schematic view of a widened groove sized to prevent the sides of the groove from impinging upon the shaft of the needle.

Referring to FIG. 15, with a groove 925 of width W, the shaft 991 of the needle 990 fits within the groove 925, without the sides 1216 of the groove 925 impinging upon the sides 993 of the shaft 991 of the needle 990. As a result, the widened width W of the groove 925 avoids undesirable effects, such as compression of the needle 990 along its axis 1001. In various embodiments, using a groove width W that is 20 percent larger than the width of the flat surface 1102 of the needle 990 at each side suitably accommodates the shaft 991 of the needle 990 within the groove 925 without the sides 1216 impinging upon the shaft 991 of the needle 990.

Figure 16:
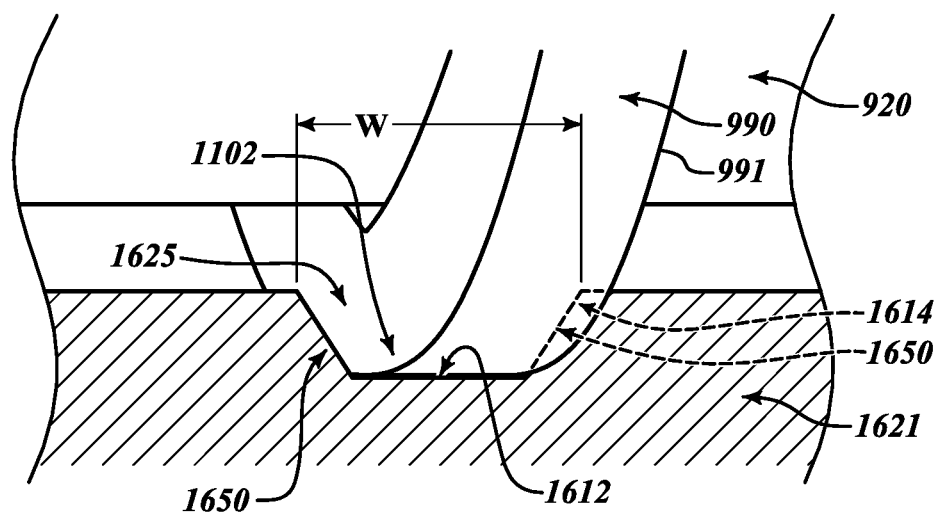
FIG. 16 is a schematic view of a groove having flared sides to prevent the sides of the groove from impinging upon the shaft of the needle.

Referring to FIG. 16, various embodiments of a grooved roller 1621 may include a groove 1625 that has two flared sides 1650 to accommodate the shaft 991 of the needle 990. Thus, as shown in FIG. 16, the groove 1625 has a generally trapezoidal cross-section. As previously described with reference to FIGS. 13-15, having a groove 925 with a width W is desirable to receive the shaft 991 of the needle 990 because the helical shape of the needle 990 causes the shaft 991 of the needle to angle toward (or into) the sides 1216 of the groove 925. The width W is used to accommodate the sides 993 of the shaft 991 of the needle 990 as the shaft 991 of the needle 990 angles away from the flat surface 1102 along the edge of the needle 990. Thus, as shown in FIG. 16, a bottom 1612 of a groove 1625 may be smaller than W, but with sides 1650 of the groove 1625 flaring from the bottom 1612 of the groove 1625 to a width W at an opening 1614 at a surface 1620 of a grooved roller 1621. The flared sides 1650 accommodate the shaft 990 of the needle 990 without impinging upon the shaft 991 to avoid applying forces to the needle 990 that may deform the needle 990 as previously described.

Figure 17:
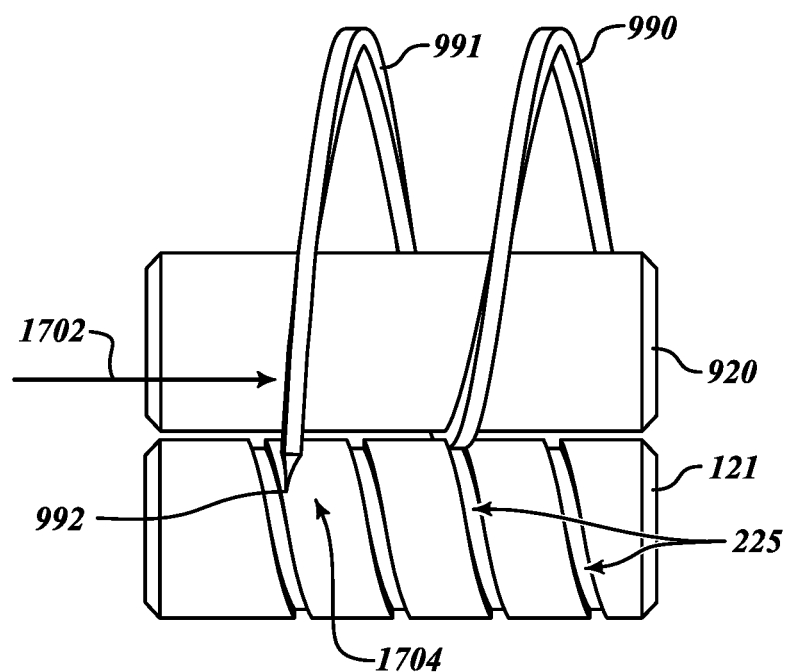
FIG. 17 is a schematic view of the rollers of the apparatus of FIG. 9 engaging the needle subject to a transverse force that compresses the needle.

Referring to FIG. 17, the force 1702 on the needle 990 also may cause the leading end 992 of the needle 991 to miss the groove 225 as the leading end 992 exits a body being sutured (not shown in FIG. 17) and revolves back toward the grooved roller 121. Instead of revolving into the groove 225, the leading end 992 of the needle 990 impacts upon a surface 1704 of the roller 121 outside of the groove 225. It will be appreciated that the force 1702 could act in either direction and thereby potentially cause the leading end 992 of the needle 990 to miss the groove 225 on either side.

Figure 18:
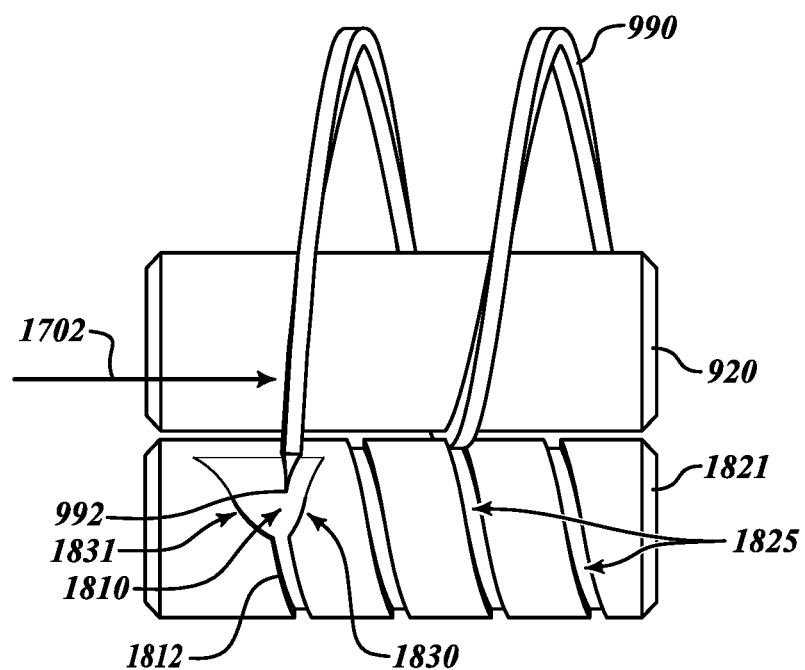
FIGS. 18-20 are schematic views of the rollers of the apparatus of FIG. 9 receiving the needle in a correcting recess.

Referring to FIG. 18, a correcting recess 1810 may be situated at a forward end 1812 of the groove 1825 of the grooved roller 1821. The correcting recess 1810 may be bounded by flared, lateral surfaces 1830 and 1831 that, as described below, will act as a funnel or guide to direct the leading end 992 of the needle 990 back into the groove 1825. The lateral sides 1830 and 1831 define a widened area to receive the leading end 992 of the needle 991. Thus, the force 1702 does not act on the needle 990 (which would cause the leading end 992 of the needle 990 to miss the groove 1825 and impact upon the surface 1704 of the roller 121). Instead, the leading end 992 of the needle is received within the correcting recess 1810. Then, as described below, the counter-rotation of the rollers 1821 and 920 will cause the correcting recess 1810 to rotate relative to the leading end 992 of the needle 990 to guide the needle 990 back into the groove 1825.

Figure 19:
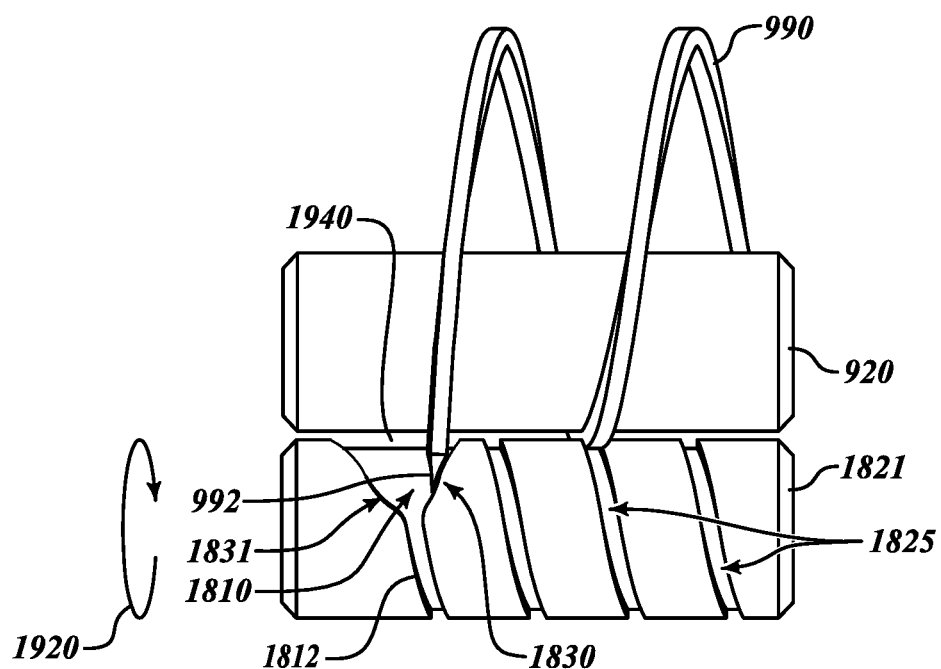

Referring to FIG. 19, as the rollers 1821 and 920 counter-rotate with the grooved roller 1821 rotating in a direction 1920, the correcting recess 1810 is rotated toward the opposing roller 920. The movement of the correcting recess 1810 results in the lateral surface 1830 of the correcting recess 1810 impinging upon the leading end 992 of the needle 990. The lateral surface 1830 moves the leading end 992 of the needle 990 in a direction 1940 to guide the leading end 992 toward the forward end 1812 of the groove 1825.

Figure 20:
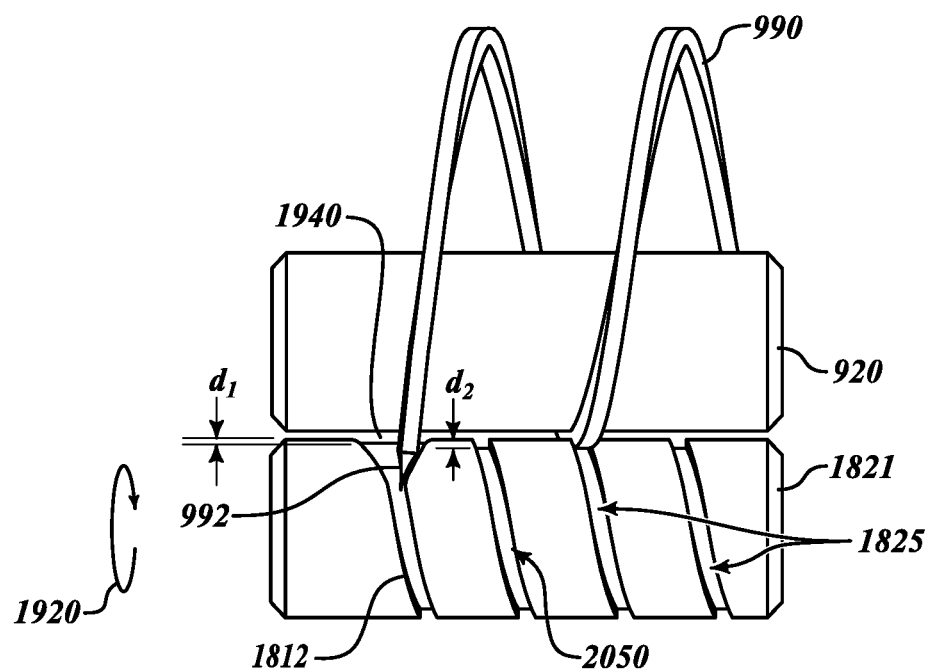

Referring to FIG. 20, with further rotation of the grooved roller 1821 in the direction 1920, the leading end 992 of the needle is guided into the forward end 1812 of the groove 1825. The correcting recess (not shown in FIG. 20) will repeatedly revolve into position to receive the leading end 992 of the needle 990 on a subsequent revolution of the needle 990 after forming an additional suture.

Still referring to FIG. 20, in various embodiments, the groove 1825 may have a reduced depth $d_1$ at or near the forward end 1812 of the groove 1825 as compared to a regular depth $d_2$ of a remaining portion 2050 of the groove 1825. The reduced depth $d_1$ at the forward end 1812 may result in a reduced clearance between the groove 1825 at the forward end 1812 and the opposing roller 920. Such reduced clearance could result in the opposing roller 920 applying higher pressure against the needle 990 at the forward end 1812 of the groove 1825. The reduced depth $d_1$ (and the resultant higher pressure) enables the rollers 920 and 1821 to securely grip the needle 990 as the needle 990 begins its next revolution after having been redirected into the groove 825 by the correcting recess 1810.

Figure 21:
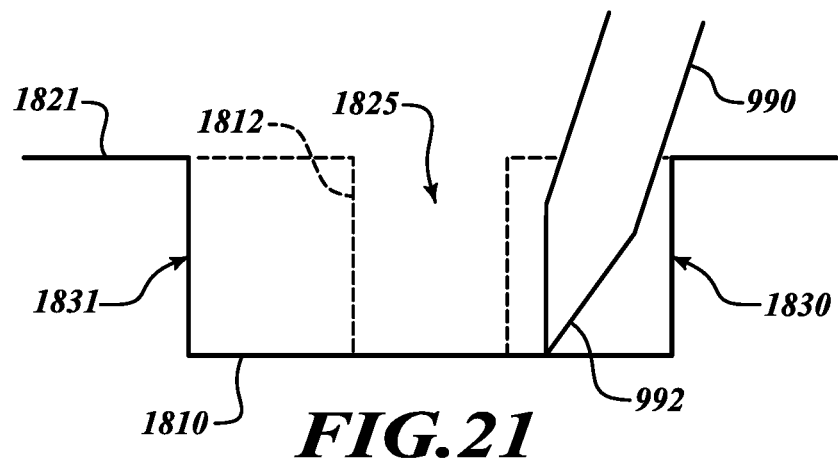
FIGS. 21-23 are side views of the needle being received by the correcting recess and guided into a groove.
Figure 22:
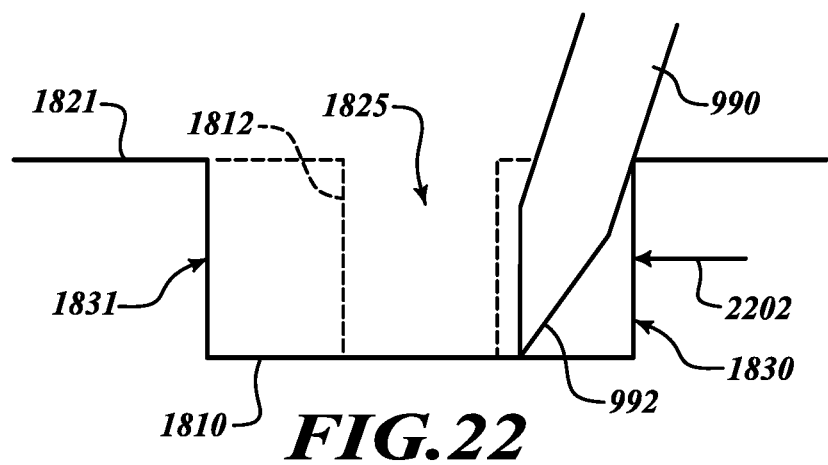
Figure 23:
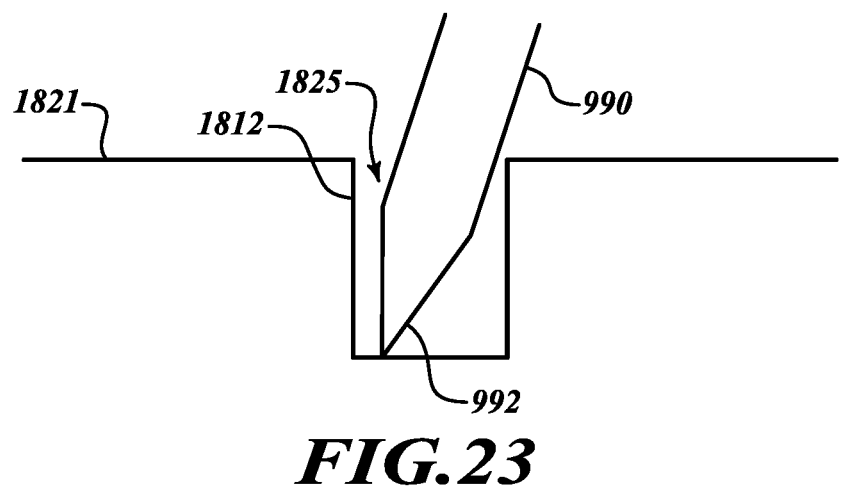

Referring to FIGS. 21-23, the leading end 992 of the needle is directed by the lateral surface 1830 of the correcting recess 1810 into the forward end 1812 of the groove 1825 of the grooved roller 1821. Referring to FIG. 21, the leading end 992 of the needle 990 is received into the correcting recess 1810 between the lateral surfaces 1830 and 1831 that define the sides of the correcting recess 1810. As previously described with reference to FIG. 18, the leading end 992 of the needle 990 would have landed outside of the groove 1825, the sides of which are represented by dotted lines in FIGS. 21-23.

Referring to FIG. 22, as the grooved roller 1821 is rotated as described with reference to FIG. 19, the lateral surface 1830 of the correcting recess 1810 engages the leading end 992 of the needle 990. It will be appreciated that, as the grooved roller 1821 is rotated as described with reference to FIG. 19, the correcting recess 1810 narrows between the lateral surfaces 1830 and 1831. Referring to FIG. 23, as the grooved roller 1821 is further rotated as described with reference to FIG. 20, the lateral surfaces 1830 and 1831 of the correcting recess 1810 (not shown in FIG. 20) merge into the forward end 1812 of the groove 1825. Thus, the correcting recess 1810 receives the leading end 992 of the needle 990 at a location outside of the groove 1825 and directs the leading end 992 of the needle 990 into the groove 1825.

Figure 24:
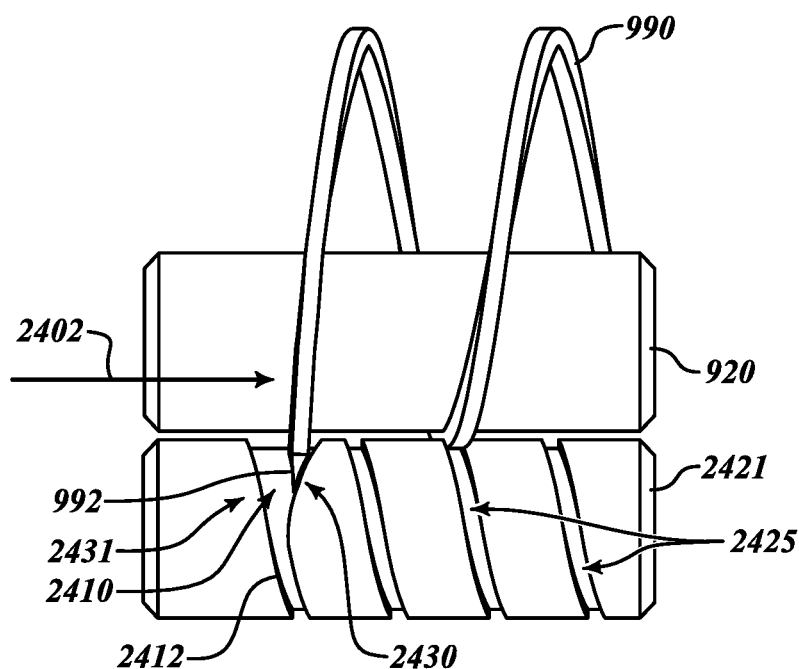
FIG. 24 are schematic views of the grooved rollers of the apparatus of FIG. 9 employing other shapes of correcting recesses.
Figure 25:
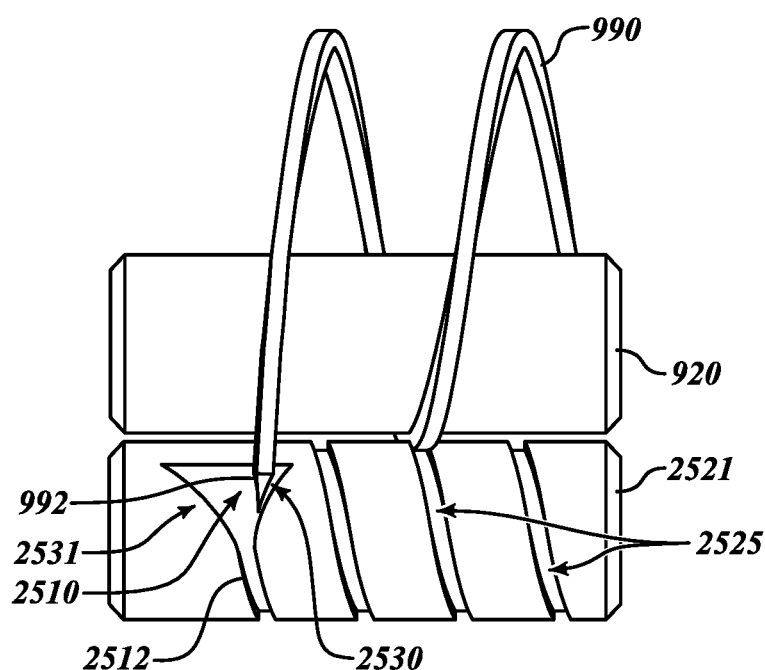
FIG. 25 is a schematic view of the rollers of the apparatus of FIG. 9 receiving the needle in another embodiment of a correcting recess.

Referring to FIGS. 24 and 25, grooved rollers may include correcting recesses in other shapes than that described with reference to FIGS. 17-23. Referring to FIG. 24, for example, the grooved roller 2421 may include a correcting recess 2410 that is only widened on one side. For example, it may be anticipated that the only forces acting on the needle 990 will deflect the needle 990 in a direction 2502. Thus, the correcting recess 2410 may include one lateral surface 2431 that extends straight from a forward end 2412 of the groove 2425 and one flared lateral surface 2430 to accommodate deflection of the leading end 992 of the needle 990 in the direction 2402. The single flared lateral surface 2430 should accommodate any anticipated deflection of the leading end 992 of the needle 990.

It will be appreciated that the lateral surfaces of the correcting recess are not limited to straight, flared shapes. Referring to FIG. 25, for example, a correcting recess 2510 may include one or more curved or other non-straight surfaces 2530 and 2531 to engage the leading end 992 of the needle 990. The curved lateral surfaces 2530 and 2531 also may serve to impinge upon the leading end 992 of the needle 990 to guide the leading end 992 into the forward end 2512 of the groove 2525. The lateral surfaces of the correcting recess are not limited to any particular geometric shape.

Figure 26A:
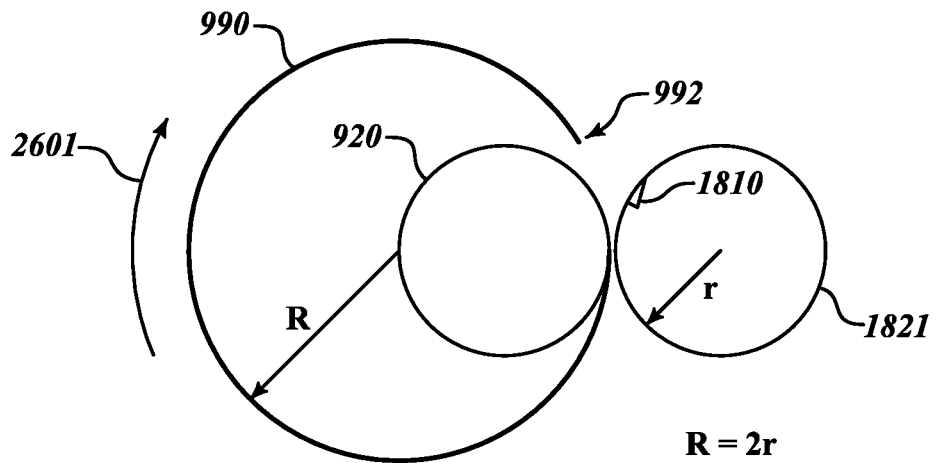
FIGS. 26A and 26B are schematic, axial views of a needle potentially missing the correcting recess on the grooved roller.
Figure 26B:
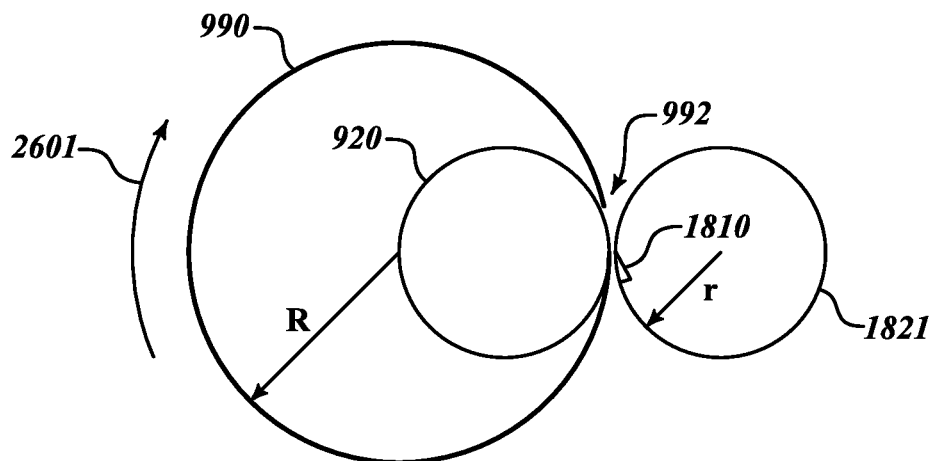

Referring to FIGS. 26A and 26B, based on forces that may affect movement of the helical needle 990, such as resistance encountered by the needle 990 or slippage of the needle 990 between rollers 920 and 1821, may cause the leading end 992 of the needle 990 to miss the correcting recess 1810 when the leading end 992 rotates toward the correcting recess 1810.

Figure 27A:
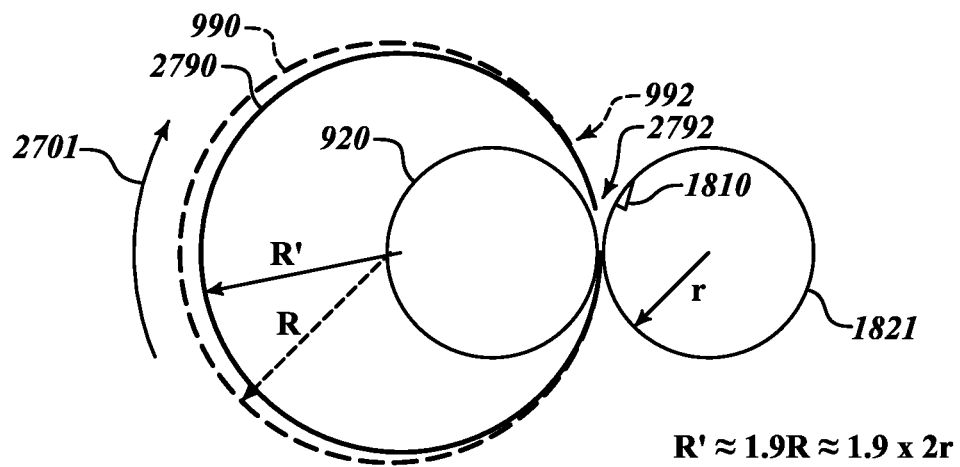
FIGS. 27A and 27B are schematic, axial views of a needle having a reduced helical radius.
Figure 27B:
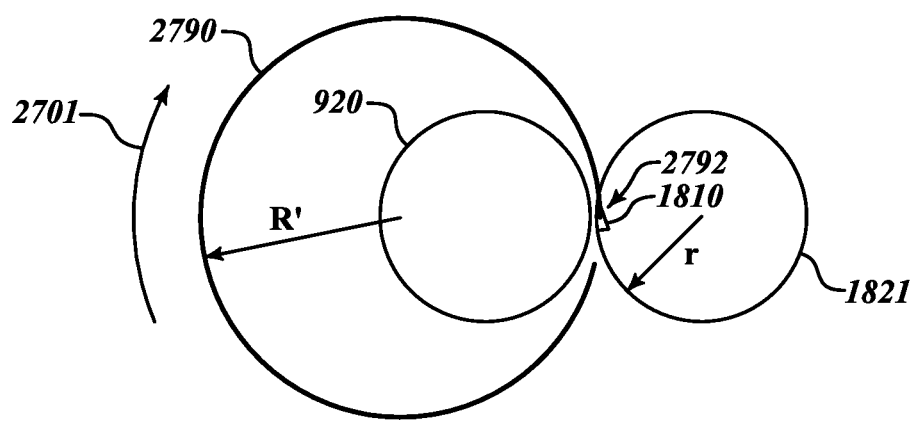

Referring to FIG. 26A, a portion of the needle 990 is depicted as the needle 990 revolves around the roller 920. It will be appreciated that the axial view of the needle 990 in FIGS. 26A, 26B, and 27A, as well as the axial views of the needle 2790 in FIGS. 27A and 27B, show a projection of the needles 990 and 2790 that describe less than a full circular arc about their axes. In practice, however, the needles 990 and 2790 actually describe more than a full circular arc around their axes to enable the rollers 920 and 1821 to engage the shafts of the needles 990 and 2790 as they are fully revolved around their axes in forming sutures.

The needles 990 and 2790 describe more than full circular arcs around their axes, in part, to account for the narrowed, sharpened leading ends 992 and 2792 of the needles 990 and 2790, respectively, which may be too narrow to be engaged by the rollers 920 and 1821. Similarly, trailing ends of the needles 990 and 2790 where the needles 990 and 2790 may be narrowed or tapered to engage the filaments they draw used to form the sutures (not shown in FIGS. 26A-27B) may be too narrow to be engaged by the rollers 920 and 1821. Accordingly, the needles 990 and 2790 describe more than full circular arcs around their axes to allow for ends that may not be engageable by the rollers 920 and 1821. In any case, the needles 990 and 2790 in FIGS. 26A-27B are represented as not describing full circular arcs around their axes to be able to show a position of the leading end 992 or 2792 of the needle 990 or 2790, respectively, without the position of the leading end 992 or 2792 potentially being obscured by an overlapping portion of the needle 990 or 2790.

Continuing to refer to FIG. 26A, as the needle 990 revolves in a direction 2601 as a result of the counter-rotation of the rollers 920 and 1821, the leading end 992 of the needle 990 approaches the correcting recess 1810 formed in the surface of the grooved roller 1821. Referring to FIG. 26B, when some forces as described have impeded movement of the needle 990, the grooved roller 1821 may have rotated such that the correcting recess 1810 has rotated such that the leading end 992 of the needle 990 is not received by the correcting recess 1810. Generally speaking, a radius R of the helical needle 990 will be a whole number multiple of the radius r of the grooved roller so that movement of the correcting recess 1810 is synchronized with the revolution of the needle 990 to receive the leading end 992 of the needle 990. In other words, a ratio between the radius R (or the diameter of the needle) of the needle 990 and the radius r (or the diameter of the needle 990) of the roller 1810 will be a whole number that is greater than or equal to two. However, forces acting on the needle 990 may impair the synchronization of the rotation of the needle 990 and the grooved roller 1810, thus indicating that the needle 990 have a radius R that may be less than a whole number multiple of the radius r of the roller 1810 (or that the ratio of R to r should be less than two or another whole number ratio of R to r).

Figure 28A:
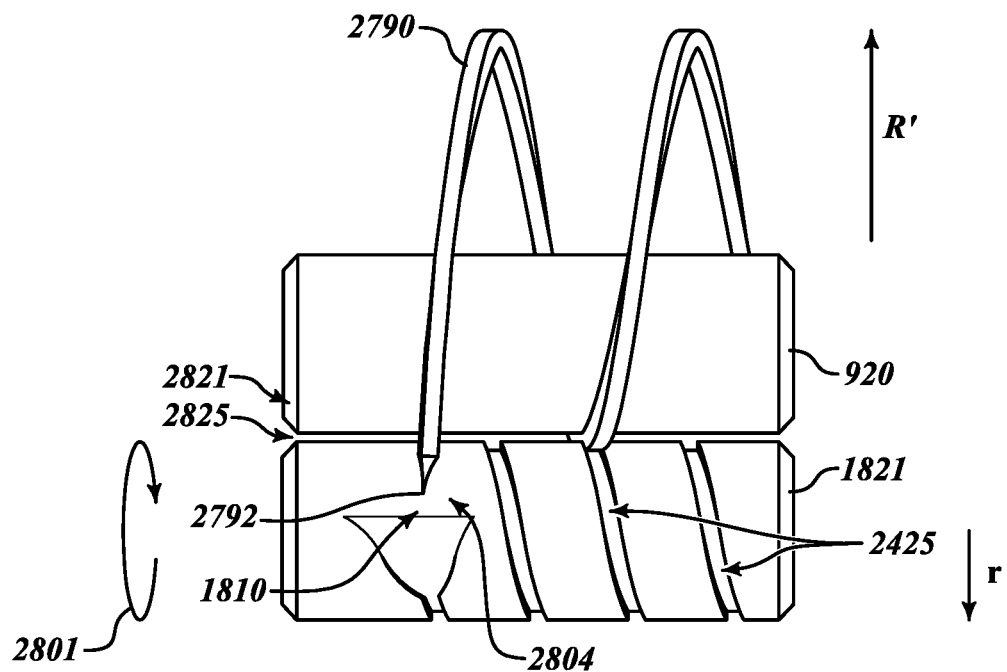
FIGS. 28A and 28B are schematic views of the needle of FIGS. 27A and 27B impacting on a surface of a grooved roller then being received in the correcting recess.
Figure 28B:
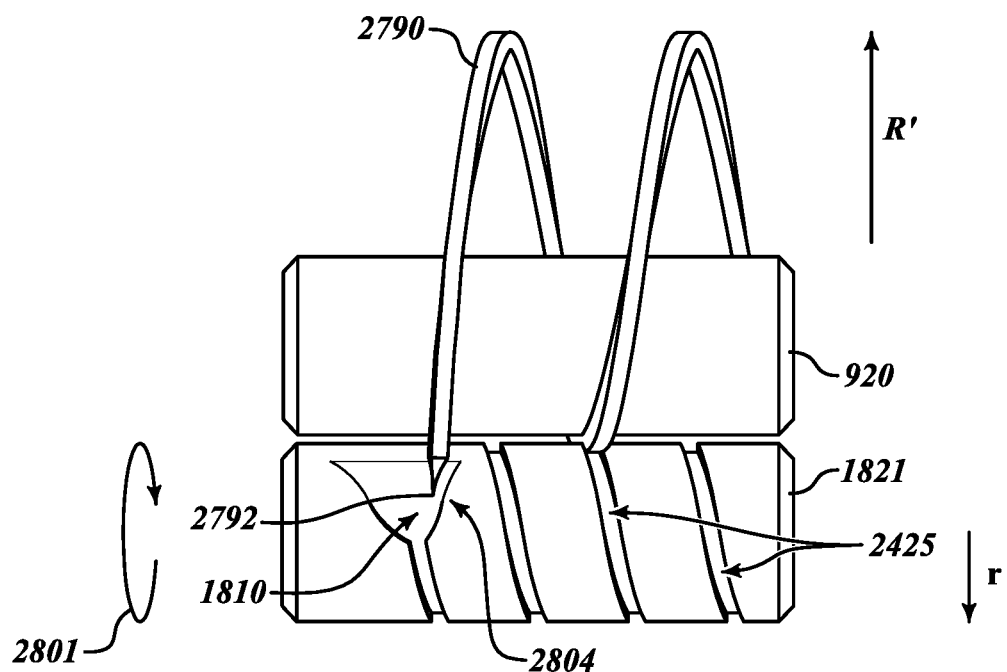

Referring to FIGS. 27A and 28B, reducing the radius of the helical needle 990 may compensate for forces that may impede rotation of the needle to avoid synchronization problems with the grooved roller 1810. Referring to FIG. 27A, the helical needle 2790 has a radius R' that is approximately five percent less than the radius R of needle 990 (represented in dashed line form in FIG. 27A for comparison with needle 2790). Thus, in contrast to the needle 990 having a radius R that is twice that of the radius r of the grooved roller 1810, the needle has a radius R' that is approximately 1.9R, or five percent less than R. Having a shortened radius R', by contrast with FIG. 26A with the needle 990 of radius R, the leading end 2792 of the needle 2790 is closer to the grooved roller 1821 at this point in the revolution of the needle 2790 than was the leading end 992 of the needle 990. Referring to FIG. 27B, as the needle 2790 revolves in a direction 2701, the leading end 2792 of the needle 2790 is received in the correcting recess 1810.

Referring to FIGS. 28A and 28B, a leading end 2792 of the needle 2790 may reach a surface 2804 of the grooved roller 1821 before the correcting recess 1810 has been rotated into position to receive the leading end 2792 of the needle 2790. Because the needle 2790 has a radius R' that is less than a whole number multiple of the radius r of the grooved roller 1810 as previously described, the needle 2790 may complete a revolution before the grooved roller with radius r, less than one-half that of the needle 2790 in this example, completes two rotations. Thus, it is possible that the leading end 2792 of the needle 2790 may reach the surface 2804 of the grooved roller 1821 before the correcting recess 1810 is in position to receive the leading end 2792 of the needle 2790. Referring to FIG. 28A, the leading end 2792 of the needle 2790 may thus impact on the surface 2804 of the grooved roller 1821 outside of the correcting recess 1810.

Referring to FIG. 28B, however, as the grooved roller 1821 continues to revolve in a direction 2801 in counterrotation with the roller 920, the correcting recess 1810 rotates under the leading end 2792 of the needle 2790. Thus, even if the leading end 2792 of the needle 2790 with radius R' should be in position to engage the correcting recess 1810 before the correcting recess 1810 is in position to receive the leading end 2792, the leading end 2792 will slide along the surface 2804 of the grooved roller 1821 until it can slide into the correcting recess 1810.

Even if the leading end 2792 should reach a gap 2825 between the surface 2804 of the grooved roller 1821 and the surface 2821 of opposing roller 920 before the leading end 2792 is received into the correcting recess 1810, the needle 2790 cannot slip into the gap 2825 between the rollers 1821 and 920. It will be recalled and appreciated that the helical needle 990 or 2790 is sized to fit between the rollers 920 or 1821 only when received within the groove 2425 of the grooved roller 1821. Accordingly, the needle 2790 is too wide to fit into the gap 2825. Thus, the leading end 2792 of the needle 2790 will slide along the surface 2804 of the grooved roller 1821 until the correcting recess 2810 rotates beneath the leading end 2792 of the needle 2790. At that point, the leading end 2792 of the needle 2790 will be captured by the correcting recess 1810 and guided into the channel 2425 as previously described with reference to FIGS. 18-25.

Figure 29:
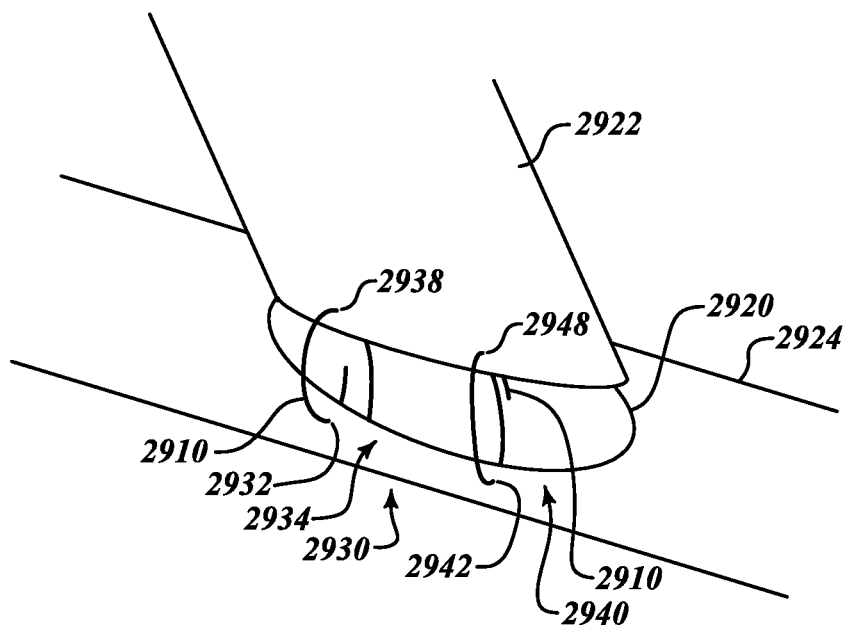
FIG. 29 is a schematic view of a helically-shaped needle being pivoted as part of joining two passages in an anastomosis procedure.

Referring to FIG. 29, a helically-shaped needle 2910 is moved around an anastomosis juncture 2920 that is being formed between a donor passage 2922 and a receiving passage 2924. It will be appreciated that the needle 2910 pivots as it is moved around the juncture 2920 to place the needle 2910 in position to suture the passages 2922 and 2924 to be joined as the needle 2910 is revolved about its axis. (The sutures, which would be drawn by the needle 2910 in a continuous strand following the path of the needle 2910, are not shown in FIG. 29.) In particular, the needle 2910 is pivoted so that its axis is generally tangential to the juncture so that revolution of the needle 2910 results in the leading end and the trailing end of the needle passing through the passages 2922 and 2924.

It will also be appreciated that, at a first position 2930, the needle 2910 pierces the receiving passage 2924 at two points 2932 and 2934 and pierces the donor passage 2922 at a single point 2938. Because the needle 2910 pierces the tissue of the receiving passage 2924 at two points 2932 and 2934, attempting to pivot the needle 2910 at the first position 2930 will involve deforming and/or stretching tissue of the receiving passage 2924, thereby possibly tearing of the tissue of the receiving passage and/or deforming the needle 2910. By contrast, at a second position 2940, the needle 2910 is revolved such that the needle 2910 pierces the tissue of the receiving passage 2924 at a single point 2942 and pierces the donor passage 2922 at a single point 2948. Because the needle 2910 pierces the tissue of each of the receiving passage 2924 and the donor passage 2922 each at one point 2942 and 2948, respectively, pivoting the needle 2910 at the second position 2940 reduces or avoids deforming or stretching tissue of the receiving passage 2924, tearing of the tissue of the receiving passage, and/or deforming the needle 2910. Thus, it is desirable to pivot the needle 2910 at positions where the needle 2910 pierces the tissue at a minimum number of points which, preferably, is only one point.

Figure 30:
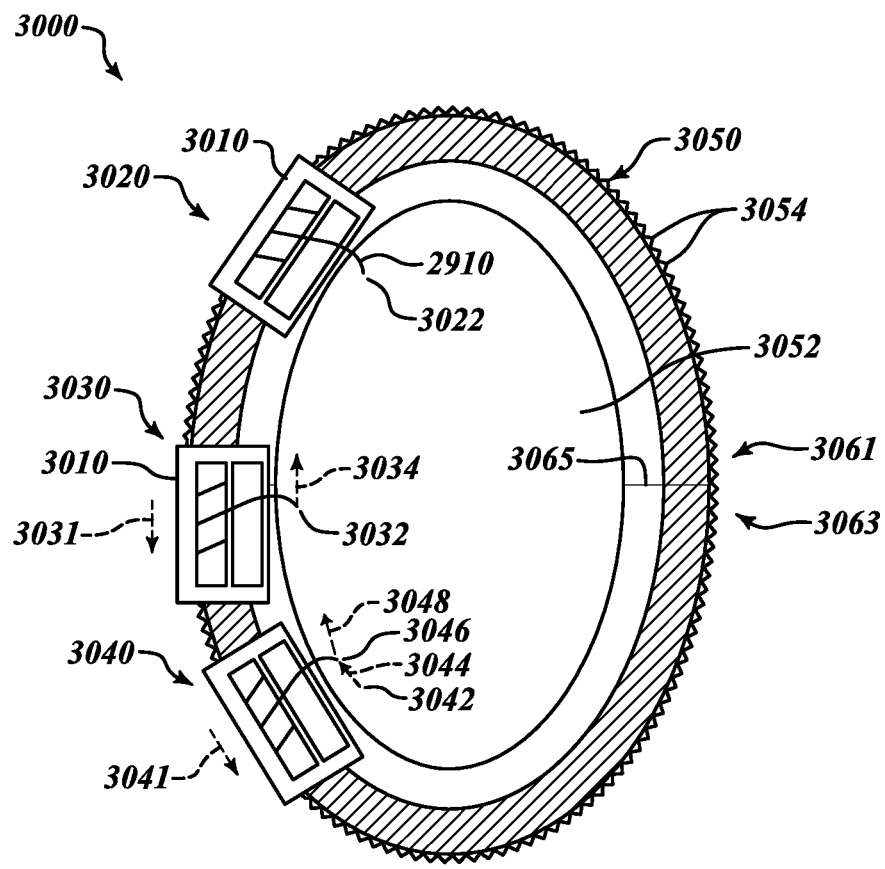
FIG. 30 is a schematic view of a suturing mechanism of FIG. 9 being rotated around a curved track.

Referring to FIG. 30, a system 3000 includes a suturing mechanism 3010 like that previously described with reference to FIG. 1. The suturing mechanism 3010 is moved around a guide track 3050 as previously described with reference to FIGS. 4-7. The suturing mechanism 3010, as previously described, drives the helically-shaped needle 2910 through tissues (not shown in FIG. 30) to form sutures. The guide track 3020 defines an opening 3052 to be situated around passages (not shown in FIG. 30) to be joined. The guide track 3020 also may include outward-facing teeth or notches to be engaged by a drive mechanism (not shown in FIG. 30) of the suturing mechanism 3010 to move the suturing mechanism 3010 around the guide track 3050. The guide track 3050 may be formed of sections 3061 and 3063 joinable at a joint 3065 to enable the guide track 3010 to be situated and/or removed from around a donor passage (as depicted in FIG. 29).

The suturing mechanism 3010 is depicted in three different locations 3020, 3030, and 3040 where the suturing mechanism is moved around the guide track 3050 and/or pivoted in forming sutures. At a first position 3020, the suturing mechanism 3010 is stationary and the needle 2910 pierces a tissue (not shown in FIG. 30) at a single point 3022. As described with reference to FIG. 29, this is a situation in which the suturing mechanism 3010 may be pivoted to reduce or avoid deforming or tearing of tissue and/or deforming the needle 2910. At a second position 3030, the suturing mechanism 3010 is moving in a direction 3031 and the needle 2910 pierces a tissue (not shown in FIG. 30) at a single point 3032. Because the suturing mechanism 3010 is moving in the direction 3031, a force 3034 between the needle 2910 and the tissue may exist which may deform the tissue and/or the needle 2910. At a third position 3040, the suturing mechanism 3010 is moving in a direction 3031 and the needle 2910 pierces a tissue (not shown in FIG. 30) at a single point 3032. The movement of the suturing mechanism 3010 moving in the direction 3041 results in forces 3044 and 3048 between the needle 2910 and the tissue at points 3042 and 3046, respectively, where the needle pierces the tissue. The multiple, nonparallel forces 3044 and 3048 may result in significant deformation of the tissue and/or the needle 2910. Thus, it will be appreciated that is desirable to pivot the suturing mechanism 3010 while the suturing mechanism 3010 is stationary or at least while the needle 2910 only pierces tissue at the single point to reduce forces that may deform tissue or the needle. Forming the guide track 3050 to facilitate selective pivoting may facilitate this process.

Figure 31:
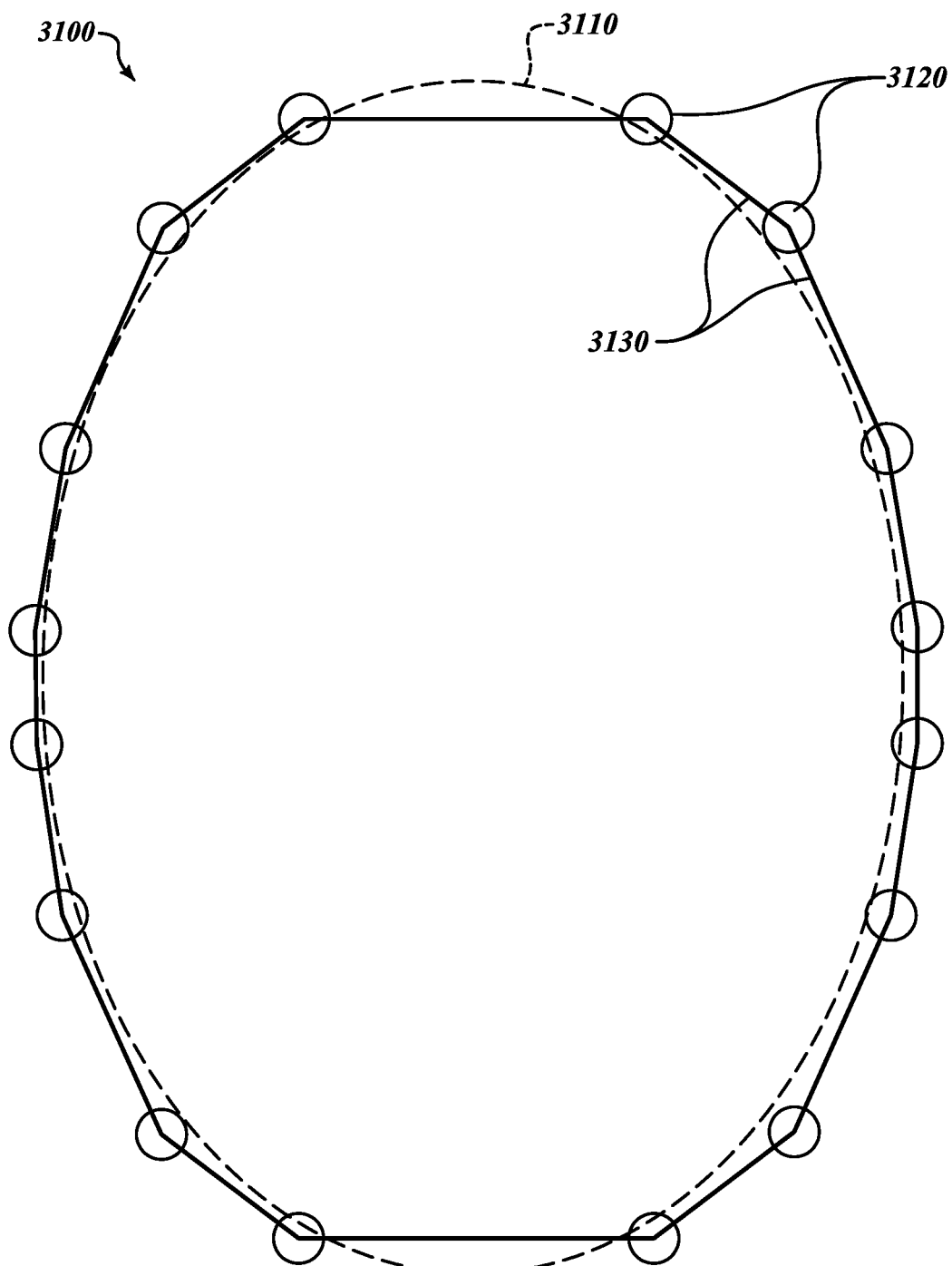
FIG. 31 is a schematic view of a representative articulated suturing path.

Referring to FIG. 31, a guide track (not shown in FIG. 31) may be formed by determining an articulated path 3100. In various embodiments, the articulated path 3100 includes a path 3110 around the objects to be sutured. In various embodiments, the path 3110 includes a number of points 3120 where the suturing mechanism (not shown in FIG. 31) is to be pivoted. These points 3120 may include locations at intervals around the path 3110 where, for example, the needle (not shown in FIG. 31) only pierces tissue at a single location. At the same time, as described with reference to FIG. 30, it is desirable to minimize movement around the periphery of the guide track while the suturing mechanism is pivoted, as described with reference to locations 2720, 2730, and 2740 and movements 2731 and 2741. Thus, the guide track is planned by starting with the points 3120 where the suturing mechanism is to be pivoted and then directed along segments 3130 between the points 3120. In practice, it may be desirable to use stepper motors to revolve the needle (not shown in FIG. 31) to form a suture, pause the suturing, then move the suturing mechanism to the next of the points 3120. The guide track may be shaped to cause the suturing mechanism to pivot at the points 3120 and direct the suturing mechanism to a next of the points, as further described below.

Figure 32:
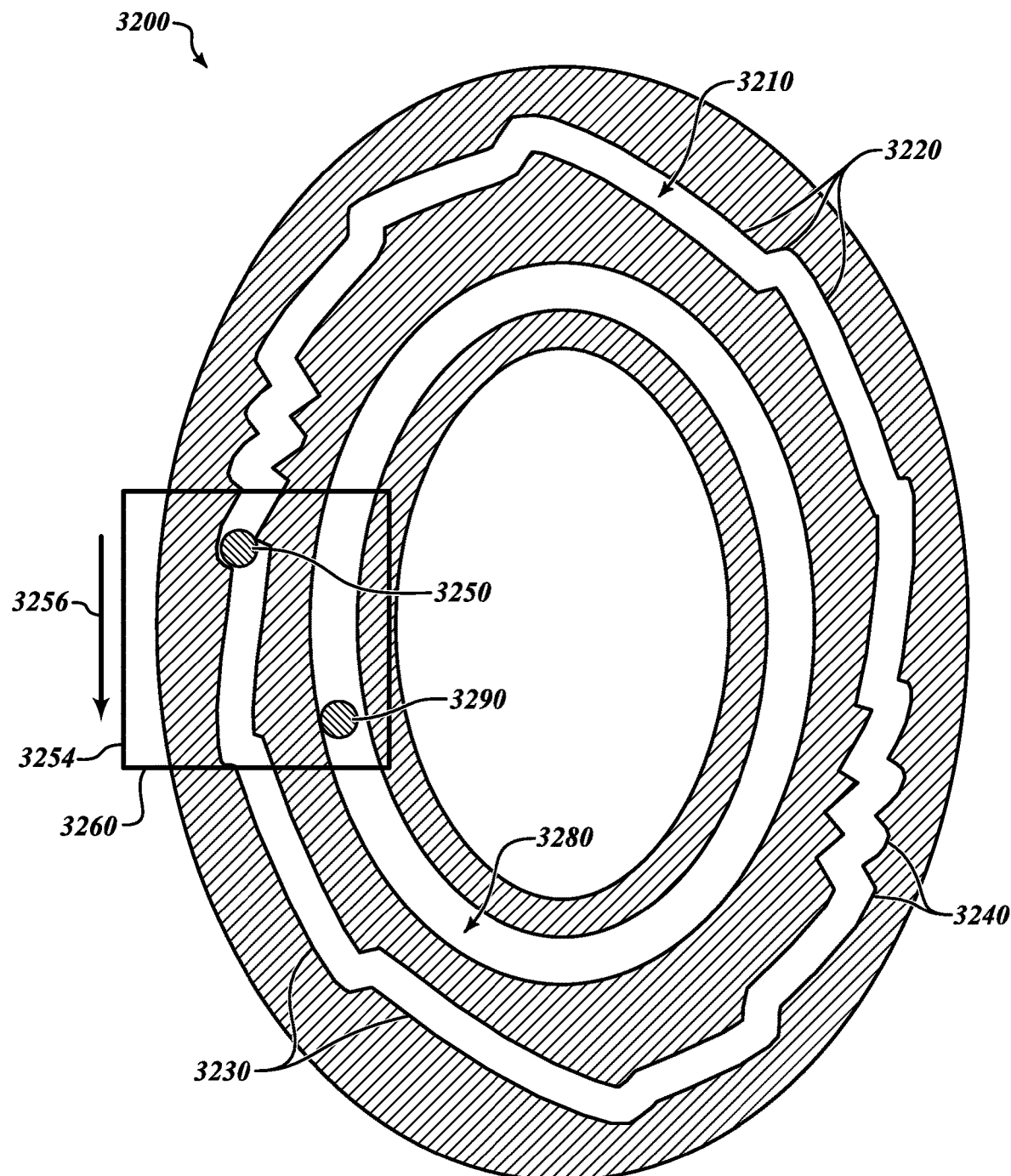
FIG. 32 is a top plan view of an illustrative guide track.

Referring to FIG. 32, a guide track 3200 defines an articulated guide channel 3210. The articulated guide channel 3210 is configured to receive and engage a first guide member 3250 that is supported by the suturing mechanism (not shown in FIG. 32). The first guide member 3250 may fixably extend directly from the suturing mechanism or may extend from a base (not shown in FIG. 32) fixably coupled with the first guide member 3250 and couplable with the suturing mechanism. An orientation of the suturing mechanism and/or the base is represented by an object 3260 in FIGS. 32-35.

The articulated guide channel 3210 includes a number of ridges 3220 around a periphery of the guide track 3200. The ridges 3220 alternately direct the guide member 3250 to move transversely and radially along the guide track 3200 in response to tangential movement 3256 imparted by a drive mechanism (not shown in FIG. 32) along an outer edge 3254 of the object 3260, thereby motivating the object 3260 around the guide track 3200.

Additionally, the guide track 3200 also may include a uniform guide channel 3280 that is configured to receive and engage a second guide member 3290. The second guide member 3290 may fixably extend directly from the suturing mechanism or may extend from the base (not shown in FIG. 32) fixably coupled with the second guide member 3250 and couplable with the suturing mechanism. The second guide member 3290 moves in an elliptical or other path around the object to be sutured. As further described below, the relative movement of the guide members 3250 and 3280 in their respective channels cause the object 3260 to translate and rotate to effect movement along the articulated path 3100 (FIG. 31). This movement along the articulated path 3100 allows the suturing mechanism (not shown) to form a suture at a point, pivot, move to the next point, and repeat the process until the juncture is sutured around its periphery.

With tangential movement 3256 imparted along the outer edge 3254 of the object 3260 by the drive mechanism, the engagement of the guide members 3250 and 3290 with the respective guide channels 3210 and 3280 directs the pivoting and the movement of the object 3260. As will be further described with reference to FIGS. 33-36, pivot portions 3230 of the ridges 3220 cause pivoting of the object 3260 and translation portions 3240 of the ridges 3220 cause radial movement of the object 3260 between the pivot points.

When the first guide member 3250 moves along one of the pivot portions 3230 of the ridges 3220, the first guide member 3250 moves both radially along the articulated guide channel 3210 and outwardly from a center of the guide track 3200. Because the first guide member 3250, in part, moves outwardly along the pivot portions 3230 while it moves radially, the second guide member 3290 (that is rigidly connected to the first guide member 3250) is generally arrested from moving through the uniform guide channel 3280. As a result, while the first guide member 3250 moves along one of the pivot portions 3230 of the ridges 3220, the object 3260 pivots about a generally stationary second guide member 3290.

By contrast, when the first guide member 3250 moves along one of the translation portions 3240 of the ridges 3220, the first guide member 3250 does not move, or moves only slightly radially, along the articulated guide channel 3210 while moving inwardly toward a center of the guide track 3200. Because the first guide member 3250, in part, moves inwardly along the translation portions 3240, the object 3260 pivots around the first guide member 3250 as the second guide member 3290 advances through the uniform guide channel 3280. As a result, while the first guide member 3250 moves along one of the translation portions 3240 of the ridges 3220, the object 3260 moves radially around the guide track 3200. Thus, the alternating pivoting and translating of the object 3260 (which is or is coupled with the suturing mechanism) effects the articulated path 3100 of FIG. 31 in directing the suturing of the object while reducing deformation of the tissue or the needle (neither of which is shown in FIG. 32).

Referring to FIGS. 33-36, engagement of the guide members 3250 and 3290 with the guide channels 3210 and 3280 provides examples of how the ridges 3220 (FIG. 32) direct the pivoting and translating of the object 3260 around the guide track. In each of FIGS. 33-36, tangential movement 3256 is applied to the object 3260 by a drive mechanism (not shown in FIGS. 33-36) as previously described with reference to FIG. 32.

Figure 33:
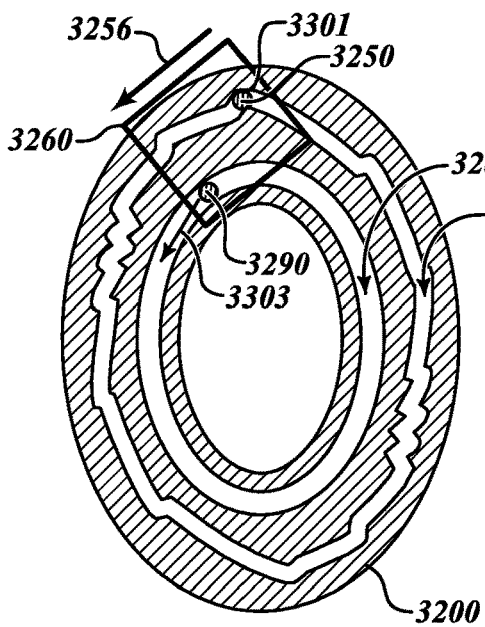
FIGS. 33-36 are schematic views of guide members causing a suturing mechanism to pivot as the suturing mechanism moves around the guide track of FIG. 32.

Referring to FIG. 33, the first guide member 3250 engages a first translation portion 3301 of one of the ridges 3220 (FIG. 32). With the tangential movement 3256 applied to the object 3260 while the first guide member 3250 is blocked from radial movement and directed to move inwardly by the first translation portion 3301, the second guide member 3290 pivots around the first guide member 3250 and moves along a segment 3303 through the uniform guide channel 3280. As a result, the object 3260 translates around the guide track to a next pivot point.

Figure 34:
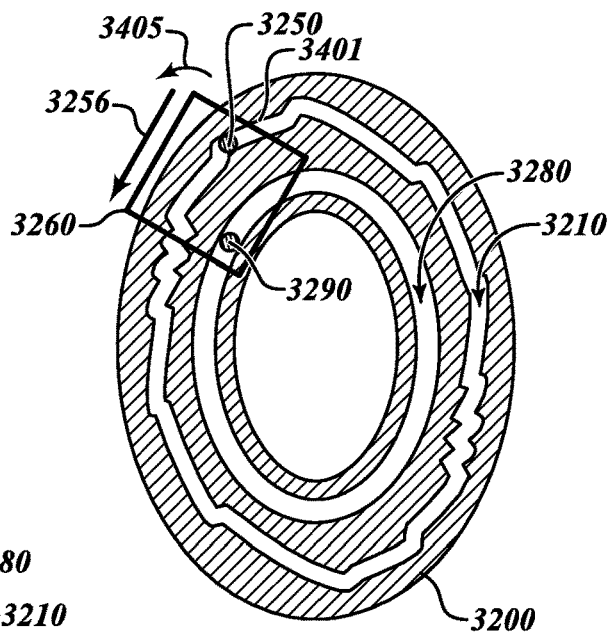

Referring to FIG. 34, the first guide member 3250 engages a first pivot portion 3401 of one of the ridges 3220 (FIG. 32). With the tangential movement 3256 applied to the object 3260 while the first guide member 3250 is directed slightly outwardly and radially along the first pivot portion 3401, the second guide member 3290 is arrested from moving forward through the uniform guide channel 3280 and the object 3260 rotates through an arc 3405. The object 3260 thus pivots around the second guide member 3200.

Figure 35:
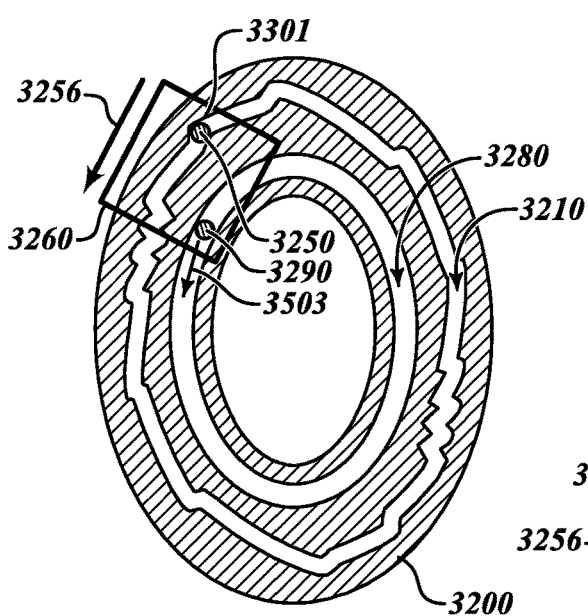

Referring to FIG. 35, the first guide member 3250 engages a second translation portion 3501 of one of the ridges 3220 (FIG. 32). With the tangential movement 3256 applied to the object 3260 while the first guide member 3250 is again blocked from radial movement and again directed to move inwardly by the first translation portion 3501, the second guide member 3290 pivots around the first guide member 3250 and moves along a segment 3503 through the uniform guide channel 3280. As a result, the object 3260 translates around the guide track to a next pivot point.

Figure 36:
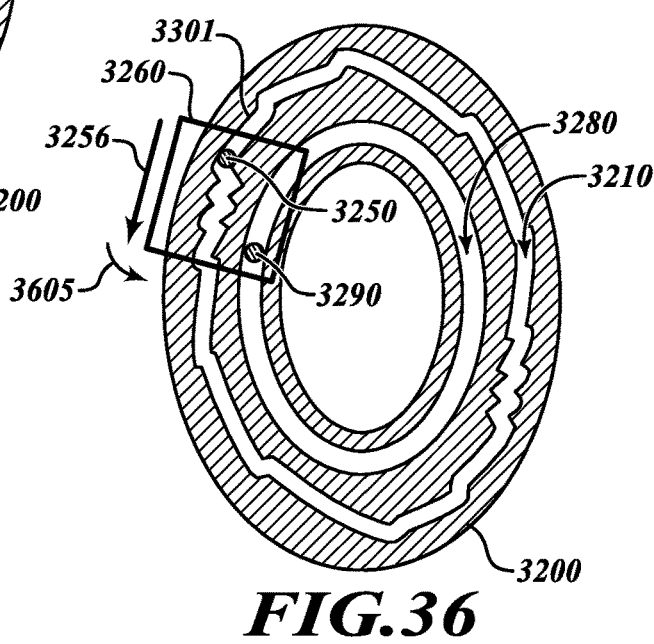

Referring to FIG. 36, the first guide member 3250 engages a second pivot portion 3601 of one of the ridges 3220 (FIG. 29). With the tangential movement 3256 applied to the object 3260 while the first guide member 3250 is again directed slightly outwardly and radially along the first pivot portion 3601, the second guide member 3290 is again arrested from moving forward through the uniform guide channel 3280 and the object 3260 rotates through an arc 3605. The object 3260 thus again pivots around the second guide member 3290. This process is repeated as the first guide member 3250 successively engages each of the alternating translation portions 23240 and pivot portions 3230 of the ridges 3220 along the articulated guide channel 3210.

Figure 37:
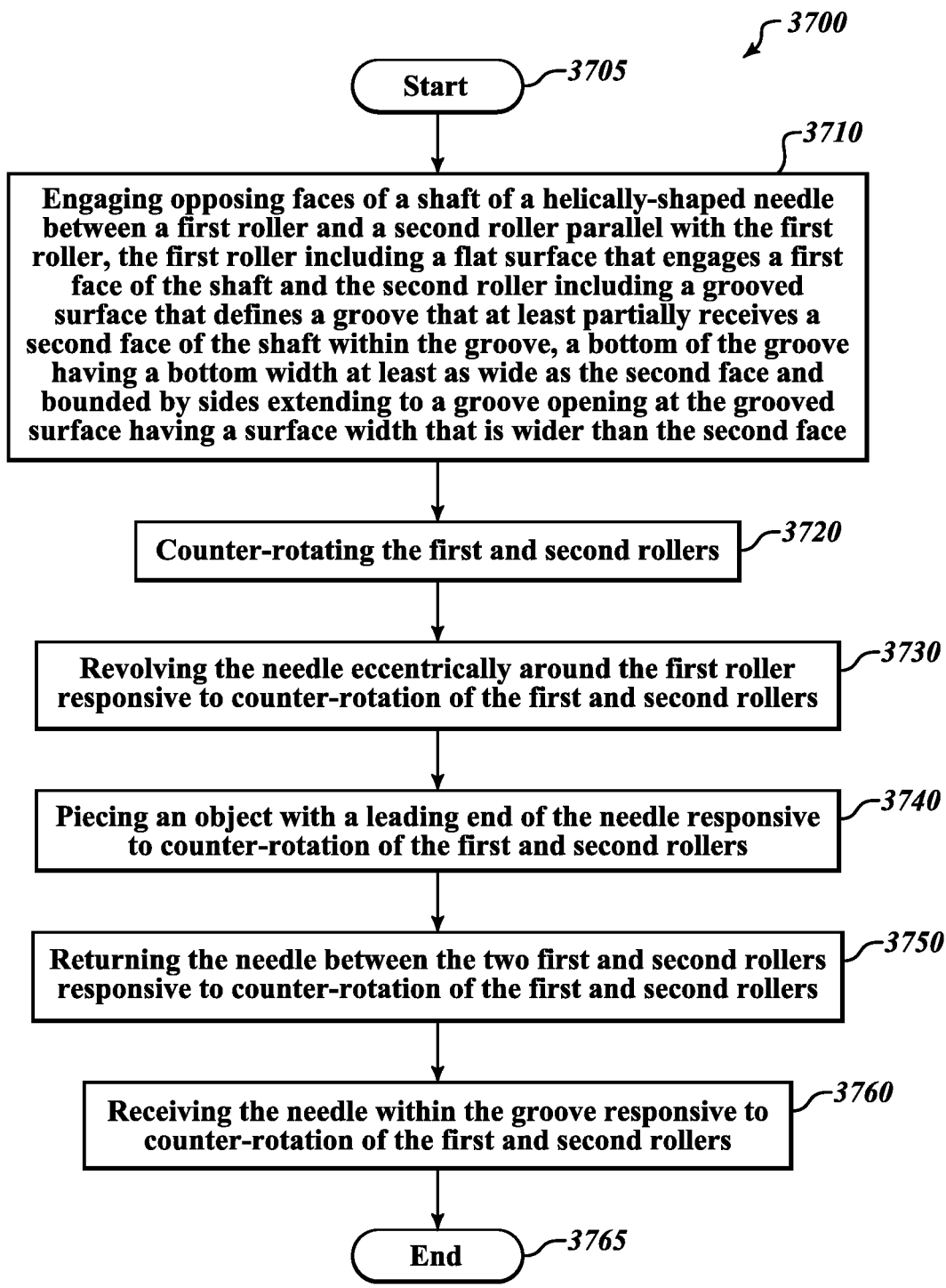
FIG. 37 is a flow diagram of an illustrative method of suturing an object.

Referring to FIG. 37, in various embodiments an illustrative method 3700 is provided for suturing an object, such as in an anastomosis, using a grooved roller having a groove with at least one flared side. The method 3700 starts at a block 3705. At a block 3710, opposing faces of a shaft of a helically-shaped needle are engaged between a first roller and a second roller parallel with the first roller. The first roller includes a flat surface that engages a first face of the shaft and the second roller includes a grooved surface that defines a groove that at least partially receives a second face of the shaft within the groove. As described with reference to FIGS. 15 and 16, a bottom of the groove has a bottom width at least as wide as the second face and bounded by sides extending to a groove opening at the grooved surface having a surface width that is wider than the second face. At a block 3720, the first and second rollers are counter-rotated. At a block 3730, the needle revolves around the first roller responsive to counter-rotation of the first and second rollers. At a block 3740, an object is pierced with a leading end of the needle responsive to counter-rotation of the first and second rollers. At a block 3750, the needle is returned between the two first and second rollers responsive to counter-rotation of the first and second rollers. At a block 3760, the needle is received within the groove responsive to counter-rotation of the first and second rollers. The method 3700 ends at a block 3765.

Figure 38:
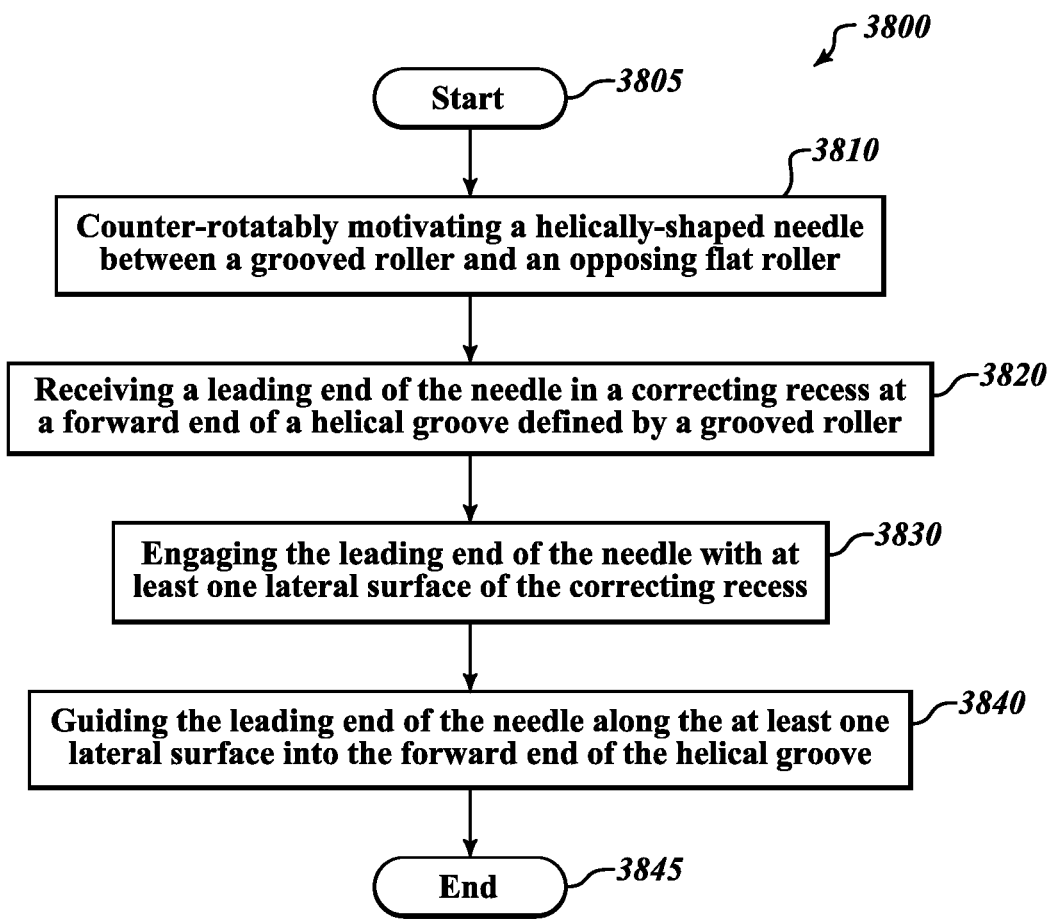
FIG. 38 is a flow diagram of another illustrative method of suturing an object.

Referring to FIG. 38, in various embodiments an illustrative method 3800 is provided for capturing a needle in a correcting recess and guiding it back into a groove of a counter-rotating roller. The method 3800 starts at a block 3805. At a block 3810, a helically-shaped needle is counter-rotatably motivated between a grooved roller and an opposing flat roller. At a block 3820, a leading end of the needle is received in a correcting recess at a forward end of a helical groove defined by a grooved roller, as previously described with reference to FIGS. 18 and 24. At a block 3830, the leading end of the needle is engaged by at least one lateral surface of the correcting recess, as previously described with reference to FIGS. 19 and 22. At a block 3740, the leading end of the needle is guided along the at least one lateral surface into the forward end of the helical groove, as previously described with reference to FIGS. 20 and 23. The method 3700 ends at a block 3845.

Figure 39:
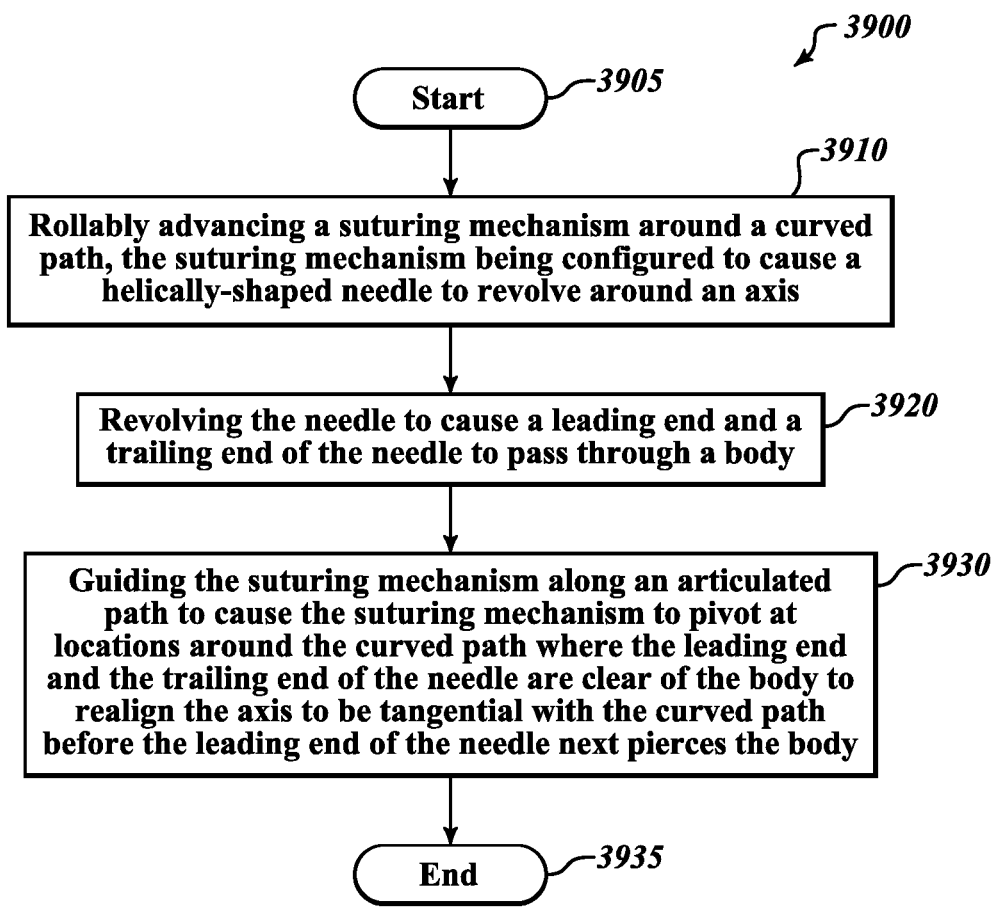
FIG. 39 is a flow diagram of another illustrative method of suturing an object.

Referring to FIG. 39, in various embodiments an illustrative method 3900 is provided for selectively pivoting and translating a suturing mechanism. The method 3900 starts at a block 3905. At a block 3910, a suturing mechanism is motivated around a curved path, with the suturing mechanism being configured to cause a helically-shaped needle to revolve around an axis. At a block 3920, the needle is revolved to cause a leading end and a trailing end of the needle to pass through a body. At a block 3930, the suturing mechanism is guided along an articulated path to cause the suturing mechanism to pivot at locations around the curved path, as previously described with reference to FIGS. 32-36. The suturing mechanism is pivoted when the leading end and the trailing end of the needle are clear of the body to realign the axis to be tangential with the curved path before the leading end of the needle next pierces the body. The method 3900 ends at a block 3935.

It will be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:

1. An apparatus comprising:
    a frame configured to counter-rotatably support two generally parallel rollers;
    a first roller supported by the frame, the first roller having a flat surface configured to rollably engage a first face of a shaft of a helically-shaped needle; and
    a second roller supported by the frame, the second roller having a grooved surface defining a helical groove that is configured to at least partially receive a second face of the shaft, wherein the second roller further defines a correcting recess bounded by lateral surfaces at a forward end of the groove that tapers to a width of the groove at the forward end of the groove, and wherein when a leading end of the helically-shaped needle is received into the correcting recess responsive to counter-rotation of the first and second rollers, at least one of the lateral surfaces engages and guides the leading end into the forward end of the groove,
    wherein the correcting recess defines a flared opening to the helical groove that includes a widened area relative to a largest width of the helical groove.

2. The apparatus of claim 1, wherein at least one of the lateral surfaces of the correcting recess tangentially diverges from an edge of the forward end of the groove.

3. The apparatus of claim 2, wherein the correcting recess is trapezoidally-shaped.

4. The apparatus of claim 1, wherein a maximum width of the correcting recess is sized to receive the leading end of the needle after deflection of the leading end resulting from at least one of deflection of the leading end upon the needle passing through an external object and deflection of the leading end caused by rotation of the frame as the needle passes through the external object.

5. The apparatus of claim 1, wherein a first depth of the groove at the forward end of the groove is shallower than a second depth of the groove toward a trailing edge of the groove.

6. The apparatus of claim 1, further comprising a rotating mechanism configured to receive a rotating member imparting a rotational force and to apply the rotational force to the rollers to cause the rollers to counter-rotate along parallel axes of rotation.

7. A system comprising:
    a helically-shaped needle, wherein the needle includes a shaft having a trailing end configured to draw a filament and a leading end shaped to pierce an object;
    a needle drive mechanism including:
        a frame configured to counter-rotatably support two generally parallel rollers;
        a first roller supported by the frame, the first roller having a flat surface configured to rollably engage a first face of a shaft of a helically-shaped needle; and
        a second roller supported by the frame, the second roller having a grooved surface defining a helical groove including straight side walls, the helical groove that ia configured to at least partially receive a second face of the shaft, wherein the second roller further defines a correcting recess bounded by lateral surfaces at a forward end of the groove that tapers to a width of the groove at the forward end of the groove, and wherein when the leading end is received into the correcting recess responsive to counter-rotation of the first and second rollers, at least one of the lateral surfaces engages and guides the leading end into the forward end of the groove; and a drive mechanism secured to the frame and configured to counter-rotate the rollers and to move the frame along an edge of an object to be sutured by the filament.

8. The system of claim 7, wherein at least one of the lateral surfaces of the correcting recess tangentially diverges from an edge of the forward end of the groove.

9. The system of claim 8, wherein the correcting recess is trapezoidally-shaped.

10. The system of claim 7, wherein a maximum width of the correcting recess is sized to receive the leading end of the helically-shaped needle after deflection of the leading end resulting from at least one of deflection of the leading end upon the needle passing through an external object and deflection of the leading end caused by rotation of the frame as the needle passes through the external object.

11. The system of claim 7, wherein a first depth of the groove at the forward end of the helical groove is shallower than a second depth of the groove toward a trailing edge of the groove.

12. The system of claim 7, wherein a radius of the helically-shaped needle is less than a whole number multiple of a radius of the second roller.

13. The system of claim 12, wherein the radius of the helically-shaped needle is approximately 5 percent less than the whole number multiple of the radius of the second roller.

14. The system of claim 7, wherein the shaft of the needle has a generally rectangular cross-section.

15. The system of claim 14, wherein the groove has one of a generally rectangular cross-section and a trapezoidally-shaped cross-section configured to receive the generally rectangular square cross-section of the shaft of the needle.

16. A method comprising:
counter-rotatably motivating a helically-shaped needle between a grooved roller and an opposing flat roller;
receiving a leading end of the needle in a correcting recess at a forward end of a helical groove defined by a grooved roller, wherein the correcting recess defines a flared opening to direct the needle into the helical groove, the flared opening includes a widened area relative to a largest width of the helical groove;
engaging the leading end of the needle with at least one lateral surface of the correcting recess; and
guiding the leading end of the needle along the at least one lateral surface into the forward end of the helical groove.

17. The method of claim 16, further comprising engaging the leading end of the needle within the correcting recess after deflection of the leading end resulting from at least one of deflection of the leading end upon the needle passing through an external object and deflection of the leading end caused by rotation of the frame as the needle passes through the external object.

18. The method of claim 16, further comprising selecting the needle to have a radius that is less than a whole number multiple of a radius of the grooved roller.

\* \* \* \* \*

UNITED STATES PATENT AND TRADEMARK OFFICE
CERTIFICATE OF CORRECTION

PATENT NO. : 11,723,652 B2
APPLICATION NO. : 17/034183
DATED : August 15, 2023
INVENTOR(S) : Adam Lee Smith It is certified that error appears in the above-identified patent and that said Letters Patent is hereby corrected as shown below:

In the Claims

In Column 20, Line 57, in Claim 7, after "groove", delete "that ia"

Signed and Sealed this
Third Day of December, 2024

Katherine Kelly Vidal
*Director of the United States Patent and Trademark Office*